United States Patent
Barnett, Jr. et al.

(10) Patent No.: US 10,426,358 B2
(45) Date of Patent: Oct. 1, 2019

(54) INTERNET OF THINGS (IOT) PERSONAL TRACKING APPARATUS, SYSTEM, AND METHOD

(71) Applicant: CenturyLink Intellectual Property LLC, Denver, CO (US)

(72) Inventors: Thomas C. Barnett, Jr., Monroe, LA (US); Kevin M. McBride, Lone Tree, CO (US); Charles I. Cook, Louisville, CO (US); Robert J. Morrill, Overland Park, KS (US)

(73) Assignee: CenturyLink Intellectual Property LLC, Broomfield, CO (US)

( * ) Notice: Subject to any disclaimer, the term of this patent is extended or adjusted under 35 U.S.C. 154(b) by 314 days.

(21) Appl. No.: 15/385,667

(22) Filed: Dec. 20, 2016

(65) Prior Publication Data

US 2018/0168464 A1  Jun. 21, 2018

(51) Int. Cl.
*H04W 4/80* (2018.01)
*A61B 5/0205* (2006.01)
(Continued)

(52) U.S. Cl.
CPC ........ *A61B 5/02055* (2013.01); *A61B 5/0022* (2013.01); *A61B 5/0024* (2013.01);
(Continued)

(58) Field of Classification Search
CPC .................................. H04W 4/28; H04W 4/70
See application file for complete search history.

(56) References Cited

U.S. PATENT DOCUMENTS 4,620,317 A   10/1986   Anderson
5,717,955 A   2/1998    Swinehart
(Continued)

FOREIGN PATENT DOCUMENTS

CN   101799987      11/2011
KR   2015-0128346 A   11/2015
(Continued)

OTHER PUBLICATIONS

International Search Report and Written Opinion prepared by the Korean Intellectual Property Office as International Searching Authority for PCT International Patent Application No. PCT/US2017/034531 dated Aug. 29, 2017; 18 pages.
(Continued)

*Primary Examiner* — Arvin Eskandarnia

(57) ABSTRACT

Novel tools and techniques are provided for implementing Internet of Things ("IoT") functionality. In some embodiments, an IoT-capable personal tracking device might receive sensor data from each of a plurality of sensors, and might analyze the sensor data to identify one or more external IoT-capable devices with which to interact and to determine one or more tasks to be performed by the identified IoT-capable devices, each based at least in part on the sensor data. In some cases, the plurality of first sensors might comprise at least one of one or more sensors that monitor physical conditions of a user's body and/or one or more sensors that monitor environmental conditions external to the user's body. The personal tracking device might subsequently autonomously send, via machine-to-machine communication, control instructions to each of the identified external IoT-capable devices, based on the determined tasks. Multiple personal tracking devices may also be used.

28 Claims, 9 Drawing Sheets

(51) Int. Cl.

| | | |
|---|---|---|
| *A61B 5/00* | (2006.01) | |
| *H04W 4/70* | (2018.01) | |
| *H04W 4/38* | (2018.01) | |
| *G16H 40/67* | (2018.01) | |
| *G16H 50/20* | (2018.01) | |
| *G16H 20/30* | (2018.01) | |
| *G16H 20/17* | (2018.01) | |
| *A61B 5/024* | (2006.01) | |
| *A61B 5/1455* | (2006.01) | |
| *A61B 5/145* | (2006.01) | |
| *A61B 5/021* | (2006.01) | |
| *A61B 5/11* | (2006.01) | |
| *A61B 5/0476* | (2006.01) | |
| *A61B 5/0402* | (2006.01) | |
| *A61B 5/08* | (2006.01) | |

(52) U.S. Cl.
CPC .......... *A61B 5/6803* (2013.01); *A61B 5/6804* (2013.01); *A61B 5/6816* (2013.01); *A61B 5/6826* (2013.01); *A61B 5/6829* (2013.01); *A61B 5/6861* (2013.01); *G16H 20/17* (2018.01); *G16H 20/30* (2018.01); *G16H 40/67* (2018.01); *G16H 50/20* (2018.01); *H04W 4/38* (2018.02); *H04W 4/70* (2018.02); *A61B 5/021* (2013.01); *A61B 5/024* (2013.01); *A61B 5/0402* (2013.01); *A61B 5/0476* (2013.01); *A61B 5/0816* (2013.01); *A61B 5/1118* (2013.01); *A61B 5/14532* (2013.01); *A61B 5/14539* (2013.01); *A61B 5/14551* (2013.01); *A61B 5/4094* (2013.01); *A61B 5/4806* (2013.01); *A61B 2560/0242* (2013.01); *A61B 2562/0219* (2013.01); *H04W 4/80* (2018.02)

(56) References Cited

U.S. PATENT DOCUMENTS

| | | | |
|---|---|---|---|
| 6,125,291 A * | 9/2000 | Miesel | A61B 5/0215 |
| | | | 600/333 |
| 6,388,399 B1 | 5/2002 | Eckel | |
| 6,792,319 B1 | 9/2004 | Bilger | |
| 7,030,781 B2 | 4/2006 | Jones | |
| 7,096,003 B2 | 8/2006 | Joao | |
| 7,397,363 B2 | 7/2008 | Joao | |
| 7,739,030 B2 | 6/2010 | Desai | |
| 8,296,383 B2 | 10/2012 | Lindahl | |
| 8,380,652 B1 | 2/2013 | Francis, Jr. | |
| 8,654,936 B1 | 2/2014 | Eslambolchi et al. | |
| 9,298,410 B2 | 3/2016 | Juchem | |
| 9,432,340 B1 | 8/2016 | Tutt et al. | |
| 9,456,276 B1 | 9/2016 | Chhetri | |
| 9,460,618 B1 | 10/2016 | Soltesz | |
| 9,536,425 B1 | 1/2017 | Soltesz | |
| 9,646,480 B2 | 5/2017 | Fadell | |
| 9,669,872 B2 | 6/2017 | Rebhan | |
| 9,672,734 B1 | 6/2017 | Ratnasingam | |
| 9,761,136 B2 | 9/2017 | Tonguz | |
| 9,860,677 B1 | 1/2018 | Agerstam | |
| 9,905,122 B2 | 2/2018 | Sloo | |
| 9,917,903 B2 | 3/2018 | Clernon | |
| 10,069,751 B2 | 9/2018 | Amulothu et al. | |
| 10,253,468 B1 | 4/2019 | Linville | |
| 2001/0029311 A1 | 10/2001 | Khare | |
| 2002/0024450 A1 | 2/2002 | Townsend | |
| 2003/0061029 A1 | 3/2003 | Shaket | |
| 2004/0083054 A1 | 4/2004 | Jones | |
| 2004/0091313 A1 | 5/2004 | Zhou | |
| 2004/0113773 A1 | 6/2004 | Nieters | |
| 2004/0142658 A1 | 7/2004 | McKenna | |
| 2004/0160319 A1 | 8/2004 | Joao | |
| 2005/0248444 A1 | 11/2005 | Joao | |
| 2006/0150644 A1 | 7/2006 | Wruck | |
| 2006/0219382 A1 | 10/2006 | Johnson | |
| 2007/0048084 A1 | 3/2007 | Jung | |
| 2007/0079113 A1 | 4/2007 | Kulkarni et al. | |
| 2007/0247794 A1 | 10/2007 | Jaffe | |
| 2008/0197204 A1 | 8/2008 | Whitney | |
| 2008/0216367 A1 | 9/2008 | Van der Poel | |
| 2008/0234878 A1 | 9/2008 | Joao | |
| 2008/0256008 A1 | 10/2008 | Kwok | |
| 2008/0300776 A1 | 12/2008 | Petrisor | |
| 2008/0303654 A1 | 12/2008 | Kates | |
| 2009/0121860 A1 | 5/2009 | Kimmel | |
| 2009/0125160 A1 | 5/2009 | Desai | |
| 2009/0134993 A1 | 5/2009 | Ashworth | |
| 2009/0327910 A1 | 12/2009 | Black | |
| 2010/0045484 A1 | 2/2010 | Brynielsson | |
| 2010/0124332 A1 | 5/2010 | Arena | |
| 2010/0217604 A1 | 8/2010 | Baldwin et al. | |
| 2010/0325421 A1 | 12/2010 | Park et al. | |
| 2011/0106321 A1 | 5/2011 | Cherian | |
| 2011/0161076 A1 | 6/2011 | Davis | |
| 2011/0288684 A1 | 11/2011 | Farlow | |
| 2012/0086563 A1 | 4/2012 | Arling | |
| 2012/0249341 A1 | 10/2012 | Brown | |
| 2012/0265370 A1 | 10/2012 | Kim | |
| 2013/0009569 A1 | 1/2013 | Knibbe | |
| 2013/0038461 A1 | 2/2013 | Hawkes | |
| 2013/0074067 A1 | 3/2013 | Chowdhry | |
| 2013/0080898 A1 | 3/2013 | Lavian | |
| 2013/0138424 A1 | 5/2013 | Koenig | |
| 2013/0217421 A1 | 8/2013 | Kim | |
| 2013/0238326 A1 | 9/2013 | Kim et al. | |
| 2013/0297199 A1 | 11/2013 | Kapp | |
| 2014/0018969 A1 | 1/2014 | Forbes | |
| 2014/0033288 A1 | 1/2014 | Wynn | |
| 2014/0146905 A1 | 5/2014 | Zavadsky | |
| 2014/0167931 A1 | 6/2014 | Lee et al. | |
| 2014/0180478 A1 | 6/2014 | Letsky | |
| 2014/0188463 A1 | 7/2014 | Noh et al. | |
| 2014/0257693 A1 | 9/2014 | Ehlers | |
| 2014/0275852 A1 * | 9/2014 | Hong | A61B 5/02427 |
| | | | 600/301 |
| 2014/0343950 A1 | 11/2014 | Simpson et al. | |
| 2015/0097686 A1 | 4/2015 | Fadell | |
| 2015/0100167 A1 | 4/2015 | Sloo | |
| 2015/0187200 A1 | 7/2015 | Fadell | |
| 2015/0249672 A1 | 9/2015 | Burns et al. | |
| 2015/0262102 A1 | 9/2015 | Tann | |
| 2015/0298654 A1 | 10/2015 | Joao | |
| 2015/0350247 A1 | 12/2015 | Adler et al. | |
| 2015/0365278 A1 | 12/2015 | Chakrabarti et al. | |
| 2016/0021127 A1 | 1/2016 | Yan | |
| 2016/0029346 A1 | 1/2016 | Suresh et al. | |
| 2016/0063857 A1 | 3/2016 | Fowe | |
| 2016/0064829 A1 | 3/2016 | Schaepperle | |
| 2016/0080322 A1 | 3/2016 | Prisser | |
| 2016/0085594 A1 | 3/2016 | Wang | |
| 2016/0093213 A1 | 3/2016 | Rider | |
| 2016/0187995 A1 | 6/2016 | Rosewall | |
| 2016/0195876 A1 | 7/2016 | Mattsson | |
| 2016/0212012 A1 | 7/2016 | Young | |
| 2016/0212613 A1 | 7/2016 | Huang | |
| 2016/0226674 A1 | 8/2016 | Kangshang et al. | |
| 2016/0248746 A1 | 8/2016 | James | |
| 2016/0267790 A1 | 9/2016 | Raamot | |
| 2016/0277310 A1 | 9/2016 | Challa | |
| 2016/0278599 A1 | 9/2016 | Seo | |
| 2016/0294828 A1 | 10/2016 | Zakaria | |
| 2016/0295364 A1 | 10/2016 | Zakaria | |
| 2016/0323271 A1 | 11/2016 | Hinman | |
| 2016/0329040 A1 | 11/2016 | Whinnery | |
| 2016/0330042 A1 | 11/2016 | Andersen | |
| 2016/0352526 A1 | 12/2016 | Adler et al. | |
| 2016/0359965 A1 | 12/2016 | Murphy et al. | |
| 2017/0006141 A1 | 1/2017 | Bhadra | |
| 2017/0006643 A1 | 1/2017 | Zakaria et al. | |
| 2017/0026157 A1 | 1/2017 | Bugenhagen et al. | |
| 2017/0026472 A1 | 1/2017 | Bugenhagen et al. | |
| 2017/0026607 A1 | 1/2017 | Kim | |

(56) References Cited

U.S. PATENT DOCUMENTS

| | | |
|---|---|---|
| 2017/0060369 A1 | 3/2017 | Goyal |
| 2017/0093866 A1 | 3/2017 | Ben-Noon |
| 2017/0110784 A1 | 4/2017 | Vermes et al. |
| 2017/0083005 A1 | 5/2017 | Hickman |
| 2017/0134937 A1 | 5/2017 | Miller |
| 2017/0141575 A1 | 5/2017 | Fulton |
| 2017/0171747 A1 | 6/2017 | Britt et al. |
| 2017/0176034 A1 | 6/2017 | Hussain |
| 2017/0181383 A1 | 6/2017 | Shen |
| 2017/0187807 A1 | 6/2017 | Clernon |
| 2017/0192437 A1 | 7/2017 | Bier |
| 2017/0195318 A1 | 7/2017 | Liu |
| 2017/0201504 A1 | 7/2017 | Funk |
| 2017/0206900 A1 | 7/2017 | Lee et al. |
| 2017/0229004 A1* | 8/2017 | Shah ............ F41H 9/10 |
| 2017/0237815 A1 | 8/2017 | Arsenault |
| 2017/0253258 A1 | 9/2017 | Bramucci |
| 2017/0274898 A1 | 9/2017 | Nakamura |
| 2017/0279620 A1 | 9/2017 | Kravitz et al. |
| 2017/0300953 A1 | 10/2017 | Kim |
| 2017/0345295 A1 | 11/2017 | Mattar |
| 2017/0345420 A1 | 11/2017 | Barnett, Jr. |
| 2017/0358025 A1 | 12/2017 | Varma |
| 2017/0371337 A1 | 12/2017 | Ramasamy |
| 2018/0040172 A1 | 2/2018 | Funk |
| 2018/0062691 A1 | 3/2018 | Barnett, Jr. |
| 2018/0084596 A1 | 3/2018 | Schwengler et al. |
| 2018/0103579 A1 | 4/2018 | Grufman |
| 2018/0113450 A1 | 4/2018 | Sherony |
| 2018/0122506 A1 | 5/2018 | Grantcharov |
| 2018/0132227 A1* | 5/2018 | Ghosh ............ H04W 72/02 |
| 2018/0174449 A1 | 6/2018 | Nguyen |
| 2018/0178781 A1 | 6/2018 | Funk et al. |
| 2018/0181091 A1 | 6/2018 | Funk et al. |
| 2018/0181094 A1 | 6/2018 | Funk et al. |
| 2018/0181095 A1 | 6/2018 | Funk et al. |
| 2018/0183685 A1 | 6/2018 | Cook |
| 2018/0183874 A1 | 6/2018 | Cook |
| 2018/0188704 A1 | 7/2018 | Cella |
| 2018/0295405 A1 | 10/2018 | Barnett, Jr. et al. |
| 2018/0299290 A1 | 10/2018 | Slavin |
| 2018/0370567 A1 | 12/2018 | Rowell |
| 2018/0374347 A1 | 12/2018 | Silver |
| 2019/0028134 A1 | 1/2019 | Barnett, Jr. |
| 2019/0035269 A1 | 1/2019 | Donovan |
| 2019/0049994 A1 | 2/2019 | Pohl |
| 2019/0073899 A1 | 3/2019 | Radomy |
| 2019/0106099 A1 | 4/2019 | Funk et al. |

FOREIGN PATENT DOCUMENTS

| | | |
|---|---|---|
| WO | WO-2009-098676 | 8/2009 |
| WO | WO-2013-058648 | 4/2013 |
| WO | WO-2017-123392 A1 | 7/2017 |

OTHER PUBLICATIONS

Di Raimondo et al., "Secure-Off the Record Messaging," 2005, 9 pages.

Borisov et al., "Off the Record Communication, or, Why Not to Use PGP," 2004, 8 pages.

Alexander et al., "Improved User Authentication in Off-the-Record Messaging," 2009, 7 pages.

Goldberg et al., "Multi-party Off-the-Record Messaging," 2007, 11 pages.

Bersch,et al., "Bimanual Robotic Cloth Manipulation for Laundry Folding," 2011, 7 pages.

International Preliminary Report on Patentability, dated Jul. 26, 2018.

International Search Report and Written Opinion prepared by the Korean Intellectual Property Office as International Searching Authority for PCT Intl Patent App. No. PCT/US2016/067938 dated Mar. 31, 2017; 11 pages.

International Preliminary Report on Patentability, PCT-US17-034531, dated Nov. 27, 2018, 15 pages.

Stedman, Ryan, et al., (2008) "A User Study of Off-the-Record Messaging," 10 pages.

* cited by examiner

INTERNET OF THINGS (IOT) PERSONAL TRACKING APPARATUS, SYSTEM, AND METHOD

CROSS-REFERENCES TO RELATED APPLICATIONS

This application may be related to each of U.S. patent application Ser. No. 14/946,540 (the "'540 Application"), filed on Nov. 19, 2015 by Michael K. Bugenhagen et al. and titled, "Customer Based Internet of Things (IOT)", which claims priority to U.S. Patent Application Ser. No. 62/196,086 (the "'086 Application"), filed Jul. 23, 2015 by Michael K. Bugenhagen et al. and titled, "Customer Based Internet of Things (IOT)"; U.S. patent application Ser. No. 14/946,548 (the "'548 Application"), filed on Nov. 19, 2015 by Michael K. Bugenhagen et al. and titled, "Customer Based Internet of Things (IOT)—Transparent Privacy Functionality", which claims priority to U.S. Patent Application Ser. No. 62/196,090 (the "'090 Application"), filed Jul. 23, 2015 by Michael K. Bugenhagen and titled, "Customer Based Internet of Things (IOT)—Transparent Privacy Functionality"; and U.S. patent application Ser. No. 15/084,805 (the "'805 Application"), filed on Mar. 30, 2016 by Tom Funk and titled, "System and Method for Implementing Secure Communications for Internet of Things (IOT) Devices", which claims priority to U.S. Patent Application Ser. No. 62/277,245 (the "'245 Application"), filed Jan. 11, 2016 by Tom Funk and titled, "IoT Security through Combining TOR Messenger with MQTT or Additional Protocols". This application may be related to U.S. patent application Ser. No. 15/370,764 (the "'764 application"), filed Dec. 6, 2016 by Thomas C. Barnett, Jr. and titled, "Internet of Things (IoT) Human Interface Apparatus, System, and Method", which claims priority to U.S. Patent Application Ser. No. 62/342,710 (the "'710 application"), filed May 27, 2016 by Thomas C. Barnett, Jr. and titled, "Internet of Things (IoT) Human Interface Apparatus, System, and Method". This application may also be related to U.S. Patent Application Ser. No. 62/397,086 (the "'7086 application"), filed Sep. 20, 2016 by Thomas Schwengler et al. and titled, "Universal Wireless Station for Multiple Simultaneous Wireless Services"and U.S. Patent Application Ser. No. 62/403,878 (the "'878 application"), filed Oct. 4, 2016 by Thomas Schwengler et al. and titled, "Universal Wireless Station for Multiple Simultaneous Wireless Services".

This application may also be related to each of U.S. patent application Ser. No. 14/678,208 (the "'208 application"), filed Apr. 3, 2015 by Michael J. Fargano et al. and titled, "Network Functions Virtualization Interconnection Gateway", which claims priority to U.S. Patent Application Ser. No. 61/974,927, filed Apr. 3, 2014 by Michael J. Fargano and titled, "Network Functions Virtualization Interconnection Gateway"; U.S. patent application Ser. No. 14/678,280 (the "'280 application"), filed on Apr. 3, 2015 by Michael J. Fargano et al. and titled, "Network Functions Virtualization Interconnection Hub", which claims priority to U.S. Patent Application Ser. No. 61/974,930, filed Apr. 3, 2014 by Michael J. Fargano and titled, "Network Functions Virtualization Interconnection Hub"; and U.S. patent application Ser. No. 14/678,309 (the "'309 application"), filed Apr. 3, 2015 by Michael J. Fargano et. al and titled, "Customer Environment Network Functions Virtualization (NFV)", which claims priority to U.S. Patent Application Ser. No. 61/976,896, filed Apr. 8, 2014 by Michael J. Fargano and titled, "Customer Environment Network Functions Virtualization (NFV)" and U.S. Patent Application Ser. No. 61/977,820, filed Apr. 10, 2014 by Michael J. Fargano and titled, "Customer Environment Network Functions Virtualization (NFV)".

This application may be related to each of U.S. patent application Ser. No. 14/730,695 (the "'695 application"), filed Jun. 4, 2015 by Charles I. Cook et al. and titled, "Remoting Application Servers", which claims priority to U.S. Patent Application Ser. No. 62/037,096, filed Aug. 13, 2014 by Charles I. Cook et al. and titled, "Remoting Application Servers"; U.S. patent application Ser. No. 14/983,884 (the "'884 application"), filed Dec. 30, 2015 by Kevin M. McBride et al. and titled, "Intent-Based Services Orchestration", which claims priority to U.S. Patent Application Ser. No. 62/233,911, filed Sep. 28, 2015 by Kevin M. McBride et al. and titled, "Intent-Based Services Orchestration" and U.S. Patent Application Ser. No. 62/247,294, filed Oct. 28, 2015 by Kevin M. McBride et al. and titled, "Intent-Based Services Orchestration"; and U.S. patent application Ser. No. 14/983,758 (the "'758 application"), filed Dec. 30, 2015 by Michael K. Bugenhagen and titled, "Virtual Machine-To-Port Peripheral Device Driver", which claims priority to U.S. Patent Application Ser. No. 62/237,981, filed Oct. 6, 2015 by Michael K. Bugenhagen and titled, "NFV Peripheral Network Driver for VNF's".

This application may also be related to each of U.S. patent application Ser. No. 15/148,688 (the "'688 application"), filed on May 6, 2016 by Charles I. Cook et al. and titled, "System and Method for Implementing Network Enhanced Gateway Functionality"; U.S. patent application Ser. No. 15/148,705 (the "'705 application"), filed on May 6, 2016 by Charles I. Cook et al. and titled, "System and Method for Implementing Extension of Customer LAN at Provider Network Service Point"; U.S. patent application Ser. No. 15/148,711 (the "'711 application"), filed May 6, 2016 by Charles I. Cook et al. and titled, "System and Method for Implementing Isolated Service Overlays between Provider Network Service Point and Customer Premises"; U.S. patent application Ser. No. 15/148,721 (the "'721 application"), filed on May 6, 2016 by Charles I. Cook et al. and titled, "System and Method for Implementing Network Experience Shifting"; and U.S. patent application Ser. No. 15/222,623 (the "'623 application"), filed Jul. 28, 2016 by Michael K. Bugenhagen et al. and titled, "System and Method for Implementing Customer Control Point or Customer Portal". Each of the '688, '705, '711, and '721 applications claim priority to each of U.S. Patent Application Ser. No. 62/157,795 (the "'795 application"), filed May 6, 2015 by Charles I. Cook et al. and titled, "NFVI Enhanced Open Business/Residential Gateways and Customer Portal", U.S. Patent Application Ser. No. 62/159,788 (the "'788 application"), filed May 11, 2015 by Charles I. Cook et al. and titled, "NFVI Enhanced Open Business/Residential Gateways and Customer Portal", U.S. Patent Application Ser. No. 62/172,359 (the "'359 application"), filed Jun. 8, 2015 by Charles I. Cook et al. and titled, "Enhanced LAN With Customer Portal Control". The '721 application further claims priority to U.S. Patent Application Ser. No. 62/299,346 (the "'346 application"), filed Feb. 24, 2016 by Charles I. Cook et al. and titled, "Experience Shifting". The '623 application claims priority to the '346 application and to U.S. Patent Application Ser. No. 62/299,357 (the "'357 application"), filed Feb. 24, 2016 by Michael K. Bugenhagen et al. and titled, "Control Point or Customer Portal".

The respective disclosures of these applications/patents (which this document refers to collectively as the "Related Applications") are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to methods, systems, apparatus, and computer software for implementing Internet of Things functionality, and, in particular embodiments, to methods, systems, apparatus, and computer software for implementing Internet of Things ("IoT") personal tracking functionality.

BACKGROUND

Although personal trackers or personal tracking devices are currently available on the market in the form of fitness trackers or activity trackers used by consumers, such conventional personal trackers or personal tracking devices do not appear to utilize full interconnectedness with other devices (and/or with external sensors) to determine actions to be taken and to identify external devices with which to interact based on sensor data obtained by the personal tracker. Such conventional personal tracking devices also do not appear to autonomously send control instructions to the identified external devices, based on the determined actions. Further, there do not appear to be any current systems that utilize multiple interconnected or interacting personal trackers for monitoring a single user, much less that such devices interact via machine-to-machine communications (e.g., IoT or the like).

Hence, there is a need for more robust and scalable solutions for implementing Internet of Things functionality, and, in particular embodiments, to methods, systems, apparatus, and computer software for implementing Internet of Things ("IoT") personal tracking functionality.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF CERTAIN EMBODIMENTS

Overview

Figure 1:
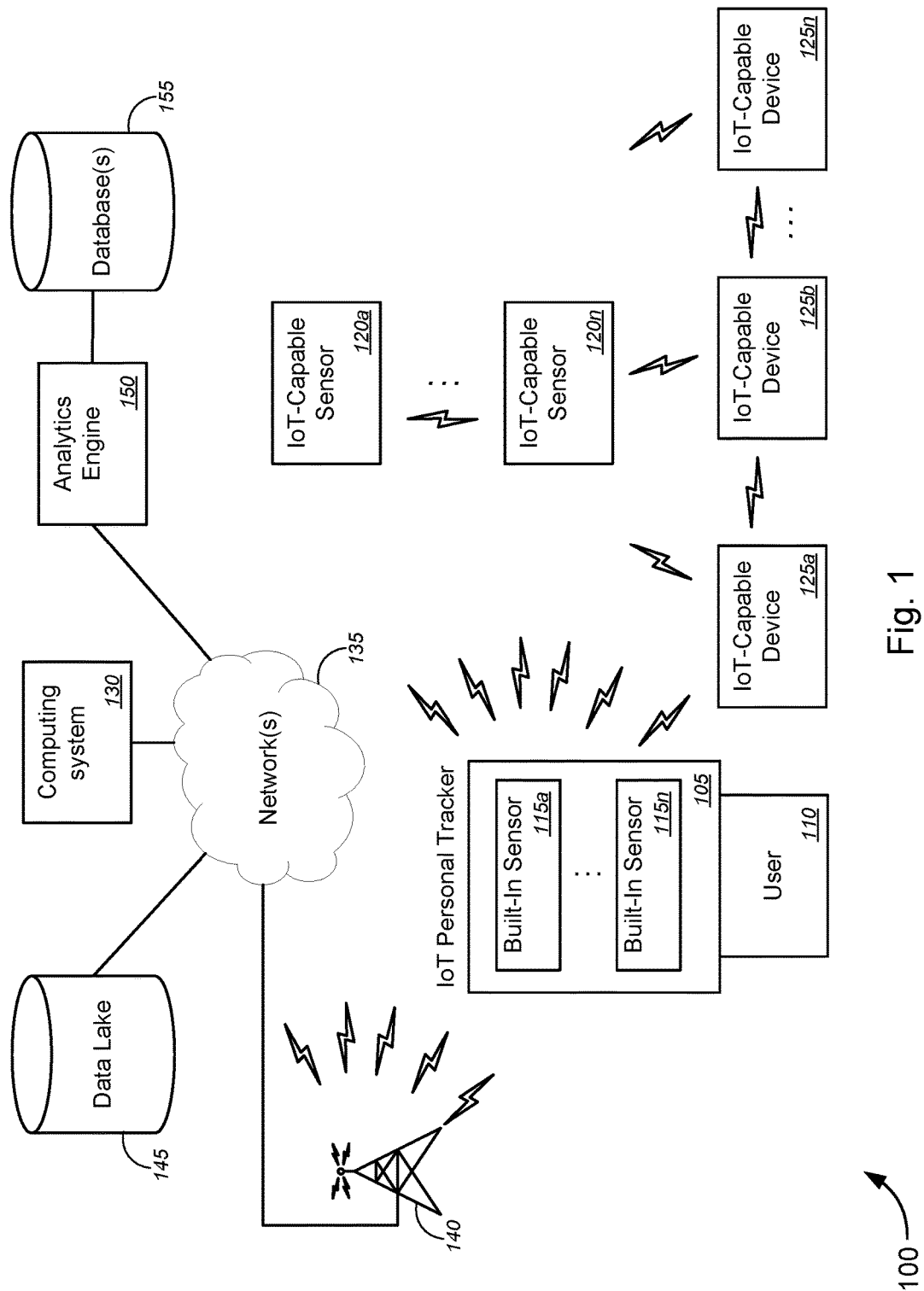
FIG. 1 is a schematic diagram illustrating a system for implementing Internet of Things ("IoT") personal tracking functionality, in accordance with various embodiments.

Various embodiments provide tools and techniques for implementing Internet of Things functionality, and, in particular embodiments, to methods, systems, apparatus, and computer software for implementing Internet of Things ("IoT") personal tracking functionality.

In various embodiments, a processor of a first IoT-capable personal tracking device might receive at least one first sensor data from each of at least one first sensor of a plurality of first sensors of the first IoT-capable personal tracking device, and might analyze the at least one first sensor data to identify one or more first external IoT-capable devices with which to interact and to determine one or more first tasks to be performed by the identified one or more first external IoT-capable devices, each based at least in part on the at least one first sensor data from each of the at least one first sensor. In some cases, the plurality of first sensors might comprise at least one of one or more second sensors that monitor physical conditions of a body of a user or one or more third sensors that monitor environmental conditions external to the body of the user. The processor of the first IoT-capable personal tracking device might subsequently autonomously send, via machine-to-machine communication, one or more first control instructions to each of the identified one or more first external IoT-capable devices, based on the determined one or more first tasks.

According to some embodiments, the first IoT-capable personal tracking device might be a wearable device that can be removably affixed to at least one of a portion of skin of the user, a limb of the user, an appendage of the user, a torso of the user, a head of the user, or a piece of clothing worn by the user, and/or the like. Alternatively, the first IoT-capable personal tracking device might be an implantable device that can be at least one of implanted under one or more layers of skin of the user, implanted within an organ of the user, implanted within a torso of the user, implanted within a head of the user, implanted within a spine of the user, implanted in an internal cavity of the user, or implanted in an external cavity of the user, and/or the like. In some embodiments, multiple IoT-capable personal tracking devices may be used to monitor the physiological conditions of the user's body and/or to monitor the environmental conditions external to the user's body, and can comprise either a plurality of wearable personal trackers, a plurality of implantable personal trackers, or a combination of at least one wearable personal tracker and at least one implantable personal tracker.

Herein, "personal tracker" or "personal tracking device" might refer to at least one of a fitness tracker, an activity tracker, a medical monitor, an environmental safety monitor, and/or the like. The fitness tracker, activity tracker, and medical monitor might be worn by, or implanted in, any person or by a patient under the care of a physician or other doctor. The environmental safety monitor might be worn by, or implanted in, people entering or working in hazardous environments, including, but not limited to, miners, astronauts, test pilots, emergency responders, deep sea explorers, oil rig workers, construction workers, volcanologists, onsite meteorologists (e.g., stormchasers, etc.), nuclear facility operators, nuclear clean-up crew members, submersible crew members, military combatants, law enforcement officers, peacekeepers, mountain climbers, canyoneers, cavers, and/or the like.

According to some embodiments, the one or more second sensors might comprise at least one of a heart rate monitor, a pulse oximeter, an oximeter, a blood glucose monitor, a blood pressure monitor, a blood flow monitor, a nitrogen monitor, a carbon dioxide monitor, a sleep monitor, an activity monitor, a step counter, one or more limb movement monitors, one or more thermometers, one or more accelerometers, one or more gyroscopes, one or more body fat monitors, one or more body muscle monitors, one or more bone density monitors, one or more pH monitors, a body fluid monitor, a brain wave monitor, a synaptic activity monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a pathogen detector, a blood tester, one or more blood alcohol level detectors, one or more drug testers, or one or more location monitors, and/or the like.

In some embodiments, the one or more third sensors might comprise at least one of an ambient temperature sensor, a flame detector, a particulate sensor, a light sensor, a humidity sensor, an air quality sensor, an atmospheric oxygen level monitor, an atmospheric carbon dioxide level monitor, an atmospheric nitrogen level monitor, an atmospheric pressure sensor, an environmental carbon monoxide sensor, a smoke detector, a gas toxicity monitor, a carcinogen detector, a radiation sensor, a location sensor, a location beacon, an object identifier beacon, a telecommunications signal sensor, a sound amplitude sensor, a frequency sensor, an accelerometer, a proximity sensor, a weather sensor, or a seismic sensor, and/or the like.

In some aspects, according to some embodiments, the one or more first external IoT-capable devices might comprise at least one of a wearable drug delivery device, an implantable drug delivery device, a medical server, a medical database, a user device associated with a physician, a user device associated with a healthcare provider, a user device associated with the user, a user device associated with a relative or guardian of the user, a user device associated with a member of an organization with which the user is affiliated (e.g., a club, a school, a company/employer, a prison, a rewards club, etc.), a user device associated with an emergency response team member, a smart medical alert bracelet, an IoT management node, an IoT human interface device, an IoT vehicle node, one or more household devices, one or more office devices, one or more lighting systems, one or more environmental control systems, one or more speakers, one or more display devices, or one or more communications systems, and/or the like.

In some embodiments, the user might interact with the IoT-capable personal tracking device via one or more of the following interface functionalities (depending upon what each particular tracking device possesses in terms of hardware, software, virtual functionalities, etc.): voice interface functionality; touch interface functionality; haptic feedback interface functionality; wireless communication interface functionality; gesture interface functionality; electrical/chemical or synaptic-simulation interface functionality; and/or the like.

According to some embodiments, a plurality of application programming interfaces ("APIs") may communicate with thousands of devices. In some cases, the IoT personal tracking device might communicate with a remote computing system that handles, coordinates, and/or manages IoT communications and interactions amongst a plurality of IoT devices (and in some instances, all IoT devices) that are communicatively coupled to the service provider network that is associated with the remote computing system and/or to any network with which the remote computing system is in communication. In some embodiments, quantum security methods may be utilized to protect data and user privacy.

In some embodiments, simple artificial intelligence ("AI") or full AI integration may be utilized within the IoT personal tracking device to aid in interactions with humans, machine-to-machine interactions, and/or other functionalities. In some instances, a set of thresholds in sensor levels of the IoT personal tracking device and/or of one or more other IoT devices to which the IoT personal tracking device is communicatively coupled may be utilized to initiate action (including, but not limited to, alerts, interpretation triggers, specific network actions, specific software/hardware actions, etc.). According to some embodiments, IPv6 identifiers may be used for each IoT device (including the IoT personal tracking device), in some cases together with other identifiers for the same device (in some cases, identification capability can simplify device registration and/or can be used for machine-to-machine communications, machine-to-network communications, etc.). In some cases, energy harvesting may be utilized to power IoT devices (including the IoT personal tracking device), either in populated areas or in remote areas. In some embodiments, the IoT personal tracking device (and/or other IoT devices communicatively coupled thereto) may be configured and/or designed to be agnostic to hardware or network of devices with which it is in communication.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The tools provided by various embodiments include, without limitation, methods, systems, and/or software products. Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible, and/or non-transitory computer readable media (such as, to name but a few examples, optical media, magnetic media, and/or the like).

Various embodiments described herein, while embodying (in some cases) software products, computer-performed methods, and/or computer systems, represent tangible, concrete improvements to existing technological areas, including, without limitation, network virtualization technology, network configuration technology, virtualized network function technology, Internet of Things ("IoT") technology, machine-to-machine communication, personal tracking technologies, user monitoring technologies, environmental monitoring technologies, and/or the like. In other aspects, certain embodiments, can improve the functioning of user equipment or systems themselves (e.g., IoT device networks, IoT devices, IoT systems, human interface devices, personal trackers, user monitoring devices, environmental monitoring systems, etc.), for example, by analyzing sensor data from either built-in IoT sensors of a personal tracking device and/or external IoT sensors, to identify one or more external IoT-capable devices with which to interact and to determine one or more tasks to be performed by the identified one or more external IoT-capable devices, by generating control instructions to the identified one or more external IoT devices to perform functions consistent with the determined tasks, and by autonomously sending, via machine-to-machine communication, the control instructions to the identified one or more external IoT devices, and/or the like. In particular, to the extent any abstract concepts are present in the various embodiments, those concepts can be implemented as described herein by devices, software, systems, and methods that involve specific novel functionality (e.g., steps or operations), such as analyzing the sensor data from the built-in and/or external IoT sensors, to identify one or more external IoT-capable devices with which to interact and to determine one or more tasks to be performed by the identified one or more external IoT-capable devices, by generating control instructions to the identified one or more external IoT devices to perform functions consistent with the determined tasks, and by autonomously sending, via machine-to-machine communication, the control instructions to the identified one or more external IoT devices, and/or the like, which improves the interaction between the user and the personal tracking device and improves the interaction between the personal tracking device and the various IoT devices in the area (i.e., around the user), improves the functionality of the personal tracking device, improves the functionality of the network of IoT devices, and/or the like, to name a few examples, that extend beyond mere conventional computer processing operations. These functionalities can produce tangible results outside of the implementing computer system, including, merely by way of example, improved functionality of the personal tracking device, improved customer experience with IoT devices and with the personal tracking device, improved lifestyle experience of the user with respect to connected devices in the user's life particularly with respect to the user's physiological and/or environmental conditions as monitored by the personal tracking device, and/or the like, at least some of which may be observed or measured by customers and/or service providers.

In an aspect, a method might comprise receiving, with a processor of a first Internet of Things ("IoT")-capable personal tracking device, at least one first sensor data from each of at least one first sensor of a plurality of first sensors of the first IoT-capable personal tracking device. The plurality of first sensors might comprise at least one of one or more second sensors that monitor physical conditions of a body of a user or one or more third sensors that monitor environmental conditions external to the body of the user. The method might also comprise analyzing, with the processor of the first IoT-capable personal tracking device, the at least one first sensor data to identify one or more first external IoT-capable devices with which to interact and to determine one or more first tasks to be performed by the identified one or more first external IoT-capable devices, each based at least in part on the at least one first sensor data from each of the at least one first sensor. The method might further comprise autonomously sending, by the processor of the first IoT-capable personal tracking device and via machine-to-machine communication, one or more first control instructions to each of the identified one or more first external IoT-capable devices, based on the determined one or more first tasks.

In some embodiments, the first IoT-capable personal tracking device might be a wearable device. In some instances, the wearable device might comprise at least one of a wrist strap, a clip, a pin, a clasp, an ear-loop, a finger ring, a toe ring, a bangle, a hook and loop-type strap, eyewear stems, a head band, or a buckle, and/or the like that allows the first IoT-capable personal tracking device to be removably affixed to at least one of a portion of skin of the user, a limb of the user, an appendage of the user, a torso of the user, a head of the user, or a piece of clothing worn by the user, and/or the like.

According to some embodiments, wherein the first IoT-capable personal tracking device might be an implantable device. In some cases, the implantable device might comprise at least one of an encapsulation layer, a membrane, a hypo-allergenic housing, a capsule, or casing, and/or the like that allows the first IoT-capable personal tracking device to be at least one of implanted under one or more layers of skin of the user, implanted within an organ of the user, implanted within a torso of the user, implanted within a head of the user, implanted within a spine of the user, implanted in an internal cavity of the user, or implanted in an external cavity of the user, and/or the like.

Merely by way of example, in some cases, the one or more second sensors might comprise at least one of a heart rate monitor, a pulse oximeter, an oximeter, a blood glucose monitor, a blood pressure monitor, a blood flow monitor, a nitrogen monitor, a carbon dioxide monitor, a sleep monitor, an activity monitor, a step counter, one or more limb movement monitors, one or more thermometers, one or more accelerometers, one or more gyroscopes, one or more body fat monitors, one or more body muscle monitors, one or more bone density monitors, one or more pH monitors, a body fluid monitor, a brain wave monitor, a synaptic activity monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a pathogen detector, a blood tester, one or more blood alcohol level detectors, one or more drug testers, or one or more location monitors, and/or the like.

In some embodiments, the one or more third sensors might comprise at least one of an ambient temperature sensor, a flame detector, a particulate sensor, a light sensor, a humidity sensor, an air quality sensor, an atmospheric oxygen level monitor, an atmospheric carbon dioxide level monitor, an atmospheric nitrogen level monitor, an atmospheric pressure sensor, an environmental carbon monoxide sensor, a smoke detector, a gas toxicity monitor, a carcinogen detector, a radiation sensor, a location sensor, a location beacon, an object identifier beacon, a telecommunications signal sensor, a sound amplitude sensor, a frequency sensor, an accelerometer, a proximity sensor, a weather sensor, or a seismic sensor, and/or the like.

According to some embodiments, the one or more first external IoT-capable devices might comprise at least one of a wearable drug delivery device, an implantable drug delivery device, a medical server, a medical database, a user device associated with a physician, a user device associated with a healthcare provider, a user device associated with the user, a user device associated with a relative or guardian of the user, a user device associated with a member of an organization with which the user is affiliated, a user device associated with an emergency response team member, a smart medical alert bracelet, an IoT management node, an IoT human interface device, an IoT vehicle node, one or more household devices, one or more office devices, one or more lighting systems, one or more environmental control systems, one or more speakers, one or more display devices, or one or more communications systems, and/or the like.

In some embodiments, the method might further comprise receiving, with at least one of the processor of the first IoT-capable personal tracking device, a processor of each of one or more second IoT-capable personal tracking devices, or a processor of a remote computing system, at least one fourth sensor data from each of at least one fourth sensor of a plurality of fourth sensors of each of the one or more second IoT-capable personal tracking devices that are separate from the first IoT-capable personal tracking device. In some cases, the plurality of fourth sensors might comprise at least one of one or more fifth sensors that monitor physical conditions of the body of the user or one or more sixth sensors that monitor environmental conditions external to the body of the user. The method might also comprise analyzing, with the at least one of the processor of the first IoT-capable personal tracking device, the processor of each of the one or more second IoT-capable personal tracking devices, or the processor of the remote computing system, a combination of the at least one first sensor data and the at least one fourth sensor data to identify one or more second external IoT-capable devices with which to interact and to determine one or more second tasks to be performed by the identified one or more second external IoT-capable devices, each based at least in part on the at least one first sensor data from the at least one first sensor of the first IoT-capable personal tracking device and the at least one fourth sensor data from each of the at least one fourth sensor of each of the one or more second IoT-capable personal tracking devices. The method might further comprise autonomously sending, by the at least one of the processor of the first IoT-capable personal tracking device, the processor of each of the one or more second IoT-capable personal tracking devices, or the processor of the remote computing system and via machine-to-machine communication, one or more second control instructions to each of the identified one or more second external IoT-capable devices, based on the determined one or more second tasks. In some instances, at least one of the one or more first external IoT-capable devices and at least one of the one or more second external IoT-capable devices might be the same external IoT-capable device. In some cases, the remote computing system might comprise at least one of a gateway device, a cloud computing system, a server in a network, a computing node in the network, or a remote computing system at a customer premises associated with the user, and/or the like.

In another aspect, a personal tracking device might comprise at least one processor, a transceiver, a plurality of first sensors, and a non-transitory computer readable medium communicatively coupled to the at least one processor. The plurality of first sensors might comprise at least one of one or more second sensors that monitor physical conditions of a body of a user or one or more third sensors that monitor environmental conditions external to the body of the user. The non-transitory computer readable medium might have stored thereon computer software comprising a set of instructions that, when executed by the at least one processor, causes the personal tracking device to: receive at least one sensor data from each of at least one sensor of a plurality of first sensors; analyze the at least one sensor data to identify one or more external Internet of Things ("IoT")-capable devices with which to interact and to determine one or more tasks to be performed by the identified one or more external IoT-capable devices, each based at least in part on the at least one sensor data from each of the at least one sensor; and autonomously send, via machine-to-machine communication through the transceiver, one or more control instructions to each of the identified one or more external IoT-capable devices, based on the determined one or more tasks.

In some embodiments, the personal tracking device might be a wearable device. In some instances, the wearable device might comprise at least one of a wrist strap, a clip, a pin, a clasp, an ear-loop, a finger ring, a toe ring, a bangle, a hook and loop -type strap, eyewear stems, a head band, or a buckle, and/or the like that allows the personal tracking device to be removably affixed to at least one of a portion of skin of the user, a limb of the user, an appendage of the user, a torso of the user, a head of the user, or a piece of clothing worn by the user, and/or the like.

According to some embodiments, wherein the personal tracking device might be an implantable device. In some cases, the implantable device might comprise at least one of an encapsulation layer, a membrane, a hypo-allergenic housing, a capsule, or casing, and/or the like that allows the personal tracking device to be at least one of implanted under one or more layers of skin of the user, implanted within an organ of the user, implanted within a torso of the user, implanted within a head of the user, implanted within a spine of the user, implanted in an internal cavity of the user, or implanted in an external cavity of the user, and/or the like.

Merely by way of example, in some cases, the one or more second sensors might comprise at least one of a heart rate monitor, a pulse oximeter, an oximeter, a blood glucose monitor, a blood pressure monitor, a blood flow monitor, a nitrogen monitor, a carbon dioxide monitor, a sleep monitor, an activity monitor, a step counter, one or more limb movement monitors, one or more thermometers, one or more accelerometers, one or more gyroscopes, one or more body fat monitors, one or more body muscle monitors, one or more bone density monitors, one or more pH monitors, a body fluid monitor, a brain wave monitor, a synaptic activity monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a pathogen detector, a blood tester, one or more blood alcohol level detectors, one or more drug testers, or one or more location monitors, and/or the like.

In some embodiments, the one or more third sensors might comprise at least one of an ambient temperature sensor, a flame detector, a particulate sensor, a light sensor, a humidity sensor, an air quality sensor, an atmospheric oxygen level monitor, an atmospheric carbon dioxide level monitor, an atmospheric nitrogen level monitor, an atmospheric pressure sensor, an environmental carbon monoxide sensor, a smoke detector, a gas toxicity monitor, a carcinogen detector, a radiation sensor, a location sensor, a location beacon, an object identifier beacon, a telecommunications signal sensor, a sound amplitude sensor, a frequency sensor, an accelerometer, a proximity sensor, a weather sensor, or a seismic sensor, and/or the like.

According to some embodiments, the one or more first external IoT-capable devices might comprise at least one of a wearable drug delivery device, an implantable drug delivery device, a medical server, a medical database, a user device associated with a physician, a user device associated with a healthcare provider, a user device associated with the user, a user device associated with a relative or guardian of the user, a user device associated with a member of an organization with which the user is affiliated, a user device associated with an emergency response team member, a smart medical alert bracelet, an IoT management node, an IoT human interface device, an IoT vehicle node, one or more household devices, one or more office devices, one or more lighting systems, one or more environmental control systems, one or more speakers, one or more display devices, or one or more communications systems, and/or the like.

In yet another aspect, a system might comprise a first personal tracking device and one or more first external IoT-capable devices. The first personal tracking device might comprise at least one first processor, a first transceiver, a plurality of first sensors, and a first non-transitory computer readable medium communicatively coupled to the at least one first processor. The plurality of first sensors might comprise at least one of one or more second sensors that monitor physical conditions of a body of a user or one or more third sensors that monitor environmental conditions external to the body of the user. The first non-transitory computer readable medium might have stored thereon computer software comprising a first set of instructions that, when executed by the at least one first processor, causes the first personal tracking device to: receive at least one first sensor data from each of at least one first sensor of the plurality of first sensors; analyze the at least one first sensor data to identify one or more first external Internet of Things ("IoT")-capable devices with which to interact and to determine one or more first tasks to be performed by the identified one or more first external IoT-capable devices, each based at least in part on the at least one first sensor data from each of the at least one first sensor; and autonomously send, via machine-to-machine communication through the first transceiver, one or more first control instructions to each of the identified the one or more first external IoT-capable devices, based on the determined one or more first tasks.

The one or more first external IoT-capable devices might each comprise a second transceiver, at least one second processor, and a second non-transitory computer readable medium communicatively coupled to the at least one second processor. The second non-transitory computer readable medium might have stored thereon computer software comprising a second set of instructions that, when executed by the at least one second processor, causes the first external IoT-capable devices to: receive, via the second transceiver, the first control instructions from the first personal tracking device and perform at least one first task of the first external IoT-capable device based on the first control instructions.

In some embodiments, the first personal tracking device might be a wearable device. In some instances, the wearable device might comprise at least one of a wrist strap, a clip, a pin, a clasp, an ear-loop, a finger ring, a toe ring, a bangle, a hook and loop-type strap, eyewear stems, a head band, or a buckle, and/or the like that allows the first personal tracking device to be removably affixed to at least one of a portion of skin of the user, a limb of the user, an appendage of the user, a torso of the user, a head of the user, or a piece of clothing worn by the user, and/or the like.

According to some embodiments, wherein the first personal tracking device might be an implantable device. In some cases, the implantable device might comprise at least one of an encapsulation layer, a membrane, a hypo-allergenic housing, a capsule, or casing, and/or the like that allows the first personal tracking device to be at least one of implanted under one or more layers of skin of the user, implanted within an organ of the user, implanted within a torso of the user, implanted within a head of the user, implanted within a spine of the user, implanted in an internal cavity of the user, or implanted in an external cavity of the user, and/or the like.

Merely by way of example, in some cases, the one or more second sensors might comprise at least one of a heart rate monitor, a pulse oximeter, an oximeter, a blood glucose monitor, a blood pressure monitor, a blood flow monitor, a nitrogen monitor, a carbon dioxide monitor, a sleep monitor, an activity monitor, a step counter, one or more limb movement monitors, one or more thermometers, one or more accelerometers, one or more gyroscopes, one or more body fat monitors, one or more body muscle monitors, one or more bone density monitors, one or more pH monitors, a body fluid monitor, a brain wave monitor, a synaptic activity monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a pathogen detector, a blood tester, one or more blood alcohol level detectors, one or more drug testers, or one or more location monitors, and/or the like.

In some embodiments, the one or more third sensors might comprise at least one of an ambient temperature sensor, a flame detector, a particulate sensor, a light sensor, a humidity sensor, an air quality sensor, an atmospheric oxygen level monitor, an atmospheric carbon dioxide level monitor, an atmospheric nitrogen level monitor, an atmospheric pressure sensor, an environmental carbon monoxide sensor, a smoke detector, a gas toxicity monitor, a carcinogen detector, a radiation sensor, a location sensor, a location beacon, an object identifier beacon, a telecommunications signal sensor, a sound amplitude sensor, a frequency sensor, an accelerometer, a proximity sensor, a weather sensor, or a seismic sensor, and/or the like.

According to some embodiments, the one or more first external IoT-capable devices might comprise at least one of a wearable drug delivery device, an implantable drug delivery device, a medical server, a medical database, a user device associated with a physician, a user device associated with a healthcare provider, a user device associated with the user, a user device associated with a relative or guardian of the user, a user device associated with a member of an organization with which the user is affiliated, a user device associated with an emergency response team member, a smart medical alert bracelet, an IoT management node, an IoT human interface device, an IoT vehicle node, one or more household devices, one or more office devices, one or more lighting systems, one or more environmental control systems, one or more speakers, one or more display devices, or one or more communications systems, and/or the like.

Merely by way of example, in some embodiments, the system might further comprise one or more second personal tracking devices that are separate from the IoT-capable personal tracking device, each second personal tracking device comprising at least one third processor, a third transceiver, a plurality of fourth sensors, and a third non-transitory computer readable medium communicatively coupled to the at least one third processor. The plurality of fourth sensors might comprise at least one of one or more fifth sensors that monitor physical conditions of a body of a user or one or more sixth sensors that monitor environmental conditions external to the body of the user. The third non-transitory computer readable medium might have stored thereon computer software comprising a third set of instructions that, when executed by the at least one third processor, causes the second personal tracking device to: receive at least one fourth sensor data from each of at least one fourth sensor of a plurality of fourth sensors; and send, via machine-to-machine communication through the third transceiver, the at least one fourth sensor data to at least one of the first personal tracking device or one or more other second personal tracking devices. At least one of the first set of instructions, when executed by the at least one first processor, might further cause the first personal tracking device or the third set of instructions, when executed by the at least one third processor, might further cause one or more of the second personal tracking devices to: receive the at least one fourth sensor data from each of the at least one fourth sensor of the plurality of fourth sensors of each of the one or more second IoT-capable personal tracking devices; analyze a combination of the at least one first sensor data and the at least one fourth sensor data to identify one or more second external IoT-capable devices with which to interact and to determine one or more second tasks to be performed by the identified one or more second external IoT-capable devices, each based at least in part on the combination of the at least one first sensor data from the at least one first sensor of the first IoT-capable personal tracking device and the at least one fourth sensor data from each of the at least one fourth sensor of each of the one or more second IoT-capable personal tracking devices; and autonomously send, via machine-to-machine communication, one or more second control instructions to each of the identified one or more second external IoT-capable devices, based on the determined one or more second tasks.

In some embodiments, the system might further comprise a remote computing system comprising at least one fourth processor and a fourth non-transitory computer readable medium communicatively coupled to the at least one fourth processor, the fourth non-transitory computer readable medium having stored thereon computer software comprising a fourth set of instructions that, when executed by the at least one fourth processor, causes the remote computing system to: receive the at least one first sensor data from each of the at least one first sensor of the plurality of first sensors of the first personal tracking device; analyze the at least one first sensor data to identify one or more third external IoT-capable devices with which to interact and to determine one or more third tasks to be performed by the identified one or more third external IoT-capable devices, each based at least in part on the at least one first sensor data from each of the at least one first sensor; and autonomously send, via machine-to-machine communication, one or more third control instructions to each of the identified one or more third external IoT-capable devices, based on the determined one or more third tasks. In some cases, the remote computing system might comprise at least one of a gateway device, a cloud computing system, a server in a network, a computing node in the network, or a remote computing system at a customer premises associated with the user, and/or the like.

Various modifications and additions can be made to the embodiments discussed without departing from the scope of the invention. For example, while the embodiments described above refer to particular features, the scope of this invention also includes embodiments having different combination of features and embodiments that do not include all of the above described features.

Specific Exemplary Embodiments

We now turn to the embodiments as illustrated by the drawings. FIGS. 1-6 illustrate some of the features of the method, system, and apparatus for implementing Internet of Things functionality, and, in particular embodiments, to methods, systems, apparatus, and computer software for implementing Internet of Things ("IoT") personal tracking functionality, as referred to above. The methods, systems, and apparatuses illustrated by FIGS. 1-6 refer to examples of different embodiments that include various components and steps, which can be considered alternatives or which can be used in conjunction with one another in the various embodiments. The description of the illustrated methods, systems, and apparatuses shown in FIGS. 1-6 is provided for purposes of illustration and should not be considered to limit the scope of the different embodiments.

With reference to the figures, FIG. 1 is a schematic diagram illustrating a system 100 for implementing Internet of Things ("IoT") personal tracking functionality, in accordance with various embodiments. In the non-limiting embodiment of FIG. 1, system 100 might include, without limitation, an IoT personal tracker or personal tracking device 105 that is either worn by or implanted in the body of a user 110, one or more Built-In IoT-capable sensors 115*a*-115*n* (collectively, "Built-In IoT-capable sensors 115," "IoT-capable sensors 115," "IoT sensors 115,"or "sensors 115"), one or more External IoT-capable sensors 120*a*-120*n* (collectively, "External IoT-capable sensors 120," "IoT-capable sensors 120," "IoT sensors 120," or "sensors 120"), and one or more IoT-capable devices 125*a,* 125*b,* through 125*n* (collectively, "IoT-capable devices 125," "IoT devices 125," or "devices 125"), and/or the like.

According to some embodiments, the one or more Built-In IoT sensors 115 (whether for an implantable or a wearable personal tracker 105) might include, without limitation, at least one of a heart rate monitor, a pulse oximeter, an oximeter, a blood glucose monitor, a blood pressure monitor, a blood flow monitor, a nitrogen monitor, a carbon dioxide monitor, a sleep monitor, an activity monitor, a step counter, one or more limb movement monitors, one or more thermometers, one or more accelerometers, one or more gyroscopes, one or more body fat monitors, one or more body muscle monitors, one or more bone density monitors, one or more pH monitors, a body fluid monitor, a brain wave monitor, a synaptic activity monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a pathogen detector, a blood tester, one or more blood alcohol level detectors, one or more drug testers, or one or more location monitors, and/or the like.

In some embodiments, the one or more Built-In IoT-capable sensors 115 or the one or more External IoT-capable sensors 120 might include, but are not limited to, at least one of an ambient temperature sensor, a flame detector, a particulate sensor, a light sensor, a humidity sensor, an air quality sensor, an atmospheric oxygen level monitor, an atmospheric carbon dioxide level monitor, an atmospheric nitrogen level monitor, an atmospheric pressure sensor, an environmental carbon monoxide sensor, a smoke detector, a gas toxicity monitor, a carcinogen detector, a radiation sensor, a location sensor, a location beacon, an object identifier beacon, a telecommunications signal sensor, a sound amplitude sensor, a frequency sensor, one or more accelerometers, one or more proximity sensors, a weather sensor, or a seismic sensor, and/or the like. According to some embodiments, rather than a sensor that senses location or other information, and the like, beacons (e.g., location beacons, object identifier beacons, and/or the like) might be used to announce (broadcast or otherwise send) information regarding a specific location, item/object, and/or the like. The IoT personal tracking device 105 and/or computing system 130 can then respond to the information sent by the beacon and take the appropriate actions.

In some instances, the one or more IoT-capable devices 125 might include, without limitation, at least one of a wearable drug delivery device, an implantable drug delivery device, a medical server, a medical database, a user device associated with a physician, a user device associated with a healthcare provider, a user device associated with the user, a user device associated with a relative or guardian of the user, a user device associated with a member of an organization with which the user is affiliated (e.g., a club, a school, a company/employer, a prison, a rewards club, etc.), a user device associated with an emergency response team member, a smart medical alert bracelet, an IoT management node, an IoT human interface device, an IoT vehicle node, one or more household devices, one or more office devices, one or more lighting systems, one or more environmental control systems, one or more speakers, one or more display devices, or one or more communications systems, and/or the like. In some cases, the at least one of the one or more sensor devices and at least one IoT-capable sensor 120 might be the same device. In some embodiments, a user device can be associated with multiple people, objects, networks, organizations, and/or the like, and the one or more IoT-capable devices 125 might further include such user devices.

According to some embodiments, system 100 might further comprise a computing system 130 that may be communicatively coupled to at least the IoT personal tracker or personal tracking device 105 (and in some cases, one or more of the sensors 115 or 120 or one or more of the devices 125) via network 135 (and in some instances, via one or more telecommunications relay systems 140). In some embodiments, the IoT personal tracking device 105 might communicate with the remote computing system 130 that handles, coordinates, and/or manages IoT communications and interactions amongst a plurality of IoT devices (and in some instances, all IoT devices) that are communicatively coupled to the service provider network that is associated with the remote computing system 130 and/or to any network with which the remote computing system 130 is in communication. In some cases, the computing system 130 might include, but is not limited to, a server computer remote from the IoT personal tracker or personal tracking device, a cloud computing system, a distributed computing system, and/or the like. In some instances, the network 135 might include, without limitation, one of a fiber network, an Ethernet network, a Token-Ring™ network, a wide-area network ("WAN"), a wireless wide area network ("WWAN"), a virtual private network ("VPN"), the Internet, an intranet, an extranet, a public switched telephone network ("PSTN"), an infra-red network, a wireless network operating under any of the IEEE 802.11 suite of protocols, the Bluetooth™ protocol known in the art, the Z-Wave protocol known in the art, the ZigBee protocol or other IEEE 802.15.4 suite of protocols known in the art, and/or any other wireless protocol, and/or any combination of these and/or other networks. In a particular embodiment, the network 135 might include an access network of the service provider (e.g., an Internet service provider ("ISP")), or the like. The one or more telecommunications relay systems 140 might include, without limitation, one or more wireless network interfaces (e.g., wireless modems, wireless access points, and the like), one or more towers, one or more satellites, and/or the like. According to some embodiments, one or more of the IoT personal tracker or personal tracking device 105, IoT-capable sensors 115 and/or 120, and/or the IoT-capable devices 125 might each comprise a software-defined multiple radio device or other multiple radio device (e.g., multiple radio devices that comprise multiple physical layer chipsets or the like) that allows each of these devices to simultaneously operate in several standards and frequencies, including, but not limited to, Wi-Fi, LTE, IoT standards (like 6LowPAN, LoRa, etc.). In this manner, these devices might each serve as an access point, small cell, and IoT base, simultaneously, with the same RF transmit stage. The multiple radio device functionality and implementation are described in detail in the '7086 and '878 applications, which have already been incorporated herein by reference in their entirety.

In some embodiments, the system 100 might further comprise a data store or data lake 145 that stores information regarding the IoT personal tracker or personal tracking device 105, information regarding the IoT-capable sensors 115 and/or 120, information regarding the IoT-capable devices 125, information regarding communications amongst these devices and sensors, information regarding data exchanged between the user 110 and the IoT personal tracker or personal tracking device 105, information regarding the network, information regarding communications between the computing system 130 and each of the IoT personal tracker or personal tracking 105, the IoT-capable sensors 115 and/or 120, and the IoT-capable devices 125, and/or the like. Any sensitive information, such as health-related information, sensor data related to physiological conditions of the user, personal information about the user, or other sensitive data might be encrypted prior to any communications with other devices, and in some cases may be encrypted prior to storing on the local data stores of the devices. In some embodiments, quantum security methods may be utilized to protect data and user privacy.

In some cases, the system 100 might further comprise an analytics engine 150 and an associated database 155 that together analyze and track (or record) non-sensitive communications amongst the various components of system 100 (i.e., the IoT personal tracker or personal tracking 105, the user 110, the IoT-capable sensors 115 and/or 120, the IoT-capable devices 125, the computing system 130, and/or the like) to identify trends as well as to identify potential issues with communications or efficiency of the system, and/or the like, the results of which might cause the computing system 130 to send software updates to affected or applicable ones of the IoT personal tracker or personal tracking 105, the IoT-capable sensors 115 and/or 120, the IoT-capable devices 125, and/or the like). In some embodiments, the database 155 might also contain profiles regarding how the IoT personal tracking device is to respond (or how IoT-capable devices are to respond) under certain conditions communicated to the analytics engine 150 from the IoT sensors 120, the IoT devices 125, and/or the IoT personal tracker 105.

The machine-to-machine communications between the IoT personal tracker or personal tracking device 105 and each of the IoT-capable sensors 115a-115n and/or 120a-120n, between the IoT personal tracker or personal tracking device 105 and each of the IoT-capable devices 125a-125n are represented in FIG. 1 by the lightning bolt symbols, which in some cases denotes wireless communications (although, in some instances, need not be wireless, but can be wired communications). In some instances, each IoT-capable device of the plurality of IoT-capable devices 125a-125n and each IoT-capable sensor of the plurality of IoT-capable sensors 115a-115n and/or 120a-120n might be assigned a unique IPv6 identifier or the like that enables secure and non-confused communications with particular IoT-capable devices or sensors (as no two devices or sensors will have the same identifier). In some cases, the IPv6 identifiers may be used together with other identifiers for the same device. In some instances, such identification capability can simplify device registration and/or can be used to facilitate machine-to-machine communications, machine-to-network communications, and/or the like.

According to some embodiments, one or more application programming interfaces ("APIs") might be established between the IoT personal tracker or personal tracking device 105 and each of the IoT-capable sensors 115a-115n and/or 120a-120n, and between the IoT personal tracker or personal tracking device 105 and each of the IoT-capable devices 125a-125n. The APIs facilitate communications with these IoT-capable devices, which could number in the thousands or more. In some embodiments, artificial intelligence ("AI") may be utilized in the IoT personal tracker or personal tracking device to improve interactions with the user, as well as improving machine-to-machine interactions between the IoT personal tracker or personal tracking device 105 and each of the IoT-capable sensors 115a-115n and/or 120a-120n, and between the IoT personal tracker or personal tracking device 105 and each of the IoT-capable devices 125a-125n, and to improve utilization of the IoT-capable sensors 115 and/or 120 and the plurality of IoT-capable devices 125, and/or the like.

In some embodiments, the IoT personal tracker or personal tracking device 105 might include, without limitation, at least one of a voice interface device (including one or more speakers and one or more microphones; for both wearable and implantable embodiments; in some cases with voice and language recognition; perhaps assisted by any AI functionality that is present in the device or the like), a button interface (for wearable embodiments), a gesture control interface (for wearable embodiments generally; with some application for implantable embodiments (e.g., where one or more sets of accelerometers, gyroscopes, location sensors (that senses or determines location based on the sensor readings), a location beacon (that sends location information to other devices, in some cases, in a broadcast, in a unicast, or in a directed transmission manner, or the like), and/or the like might be implanted in limbs or appendages (e.g., fingers, hands, forearms, toes, feet, legs, head, etc.) to record particular motions or gestures that can be designated as command gestures; etc.)), a touchscreen user interface (for wearable embodiments), a display interface (for wearable embodiments), a haptic feedback interface (for both wearable and implantable embodiments), an electrical/chemical or synaptic-simulation interface (for implantable embodiments), a wireless communications interface (for both wearable and implantable embodiments; that can communicate with one or more user devices associated with the user), and/or the like. In other words through one or more of voice interactions, physical interactions, synaptic interactions, gesture interactions, and/or user device interactions, or the like, the user can communicate with and interact with the personal tracker 105 to provide information to the personal tracker, to provide commands to the personal tracker, to receive sensor data or analyses of sensor data, to receive alerts, to receive feedback or suggestions, and/or the like.

In operation, the IoT personal tracking device 105 might receive at least one sensor data from each of at least one sensor of the one or more IoT-capable sensors 115a-115n and/or 120a-120n. The personal tracking device 105 might analyze the at least one sensor data to identify at least one IoT-capable device 125 of the one or more IoT-capable devices 125a-125n with which to interact and to determine one or more tasks to be performed by the identified at least one IoT-capable device 125, each based at least in part on the at least one sensor data from each of the at least one sensor. The personal tracking device 105 might subsequently autonomously send, via machine-to-machine communication, one or more control instructions to each of the identified at least one IoT-capable device 125, based on the determined one or more tasks. In some cases, the one or more IoT-capable devices 125a-125n might comprise one or more user devices associated with the user, including, but not limited to, a tablet computer, a smart phone, a smart watch, a mobile phone, a personal digital assistant, a desktop computer, a television, a set-top box, a gaming console, a portable gaming device, a human interface device (such as the IoT human interface device as described in detail in the '028400US and '710 applications, which have already been incorporated herein by reference in their entirety), and/or the like. According to some embodiments, the IoT personal tracking device 105 might interact with remote display devices on or around the user (including, but not limited to, a smart watch, a smart phone, a virtual reality display, an augmented reality display, a laptop computer, a tablet computer, a computer monitor, a television, and/or the like) to provide alerts, notifications, and/or the like to the user based on the sensor data collected by the sensors of the IoT personal tracking device 105. In some cases, such interactions might utilize a local wireless interface, including, without limitation, 2.4 GHz or 5 GHz WiFi, Bluetooth, Z-wave, ZigBee, etc. In some instances, the processor of the IoT personal tracking device 105 might enable proper HTML formatted outputs or the like when sending the alerts, notifications, etc. to the remote display devices for display.

Herein, "personal tracker" or "personal tracking device" might refer to at least one of a fitness tracker, a smart watch, an activity tracker, a medical monitor, an environmental safety monitor, and/or the like. The fitness tracker, activity tracker, and medical monitor might be worn by, or implanted in, any person or by a patient under the care of a physician or other doctor. The environmental safety monitor might be worn by, or implanted in, people entering or working in hazardous environments, including, but not limited to, miners, astronauts, test pilots, emergency responders, deep sea explorers, oil rig workers, construction workers, volcanologists, onsite meteorologists (e.g., stormchasers, etc.), nuclear facility operators, nuclear clean-up crew members, submersible crew members, military combatants, law enforcement officers, peacekeepers, mountain climbers, canyoneers, cavers, and/or the like.

In some aspects, the personal tracking device 105 with its suite of sensors might provide further more accurate and more interactive fitness or activity tracking. For example, as a simplistic example, the personal tracking device 105 might monitor at least one of the heart rate, the blood pressure, the respiration, the movements of the user, the posture of the user, the level of lactic acid buildup, the level of pain felt by the user, and/or the like, using a heart rate monitor, a blood pressure monitor, a respiration monitor, accelerometers and/or gyroscopes, one or more location or relative position sensors, one or more pH monitors, one or more pain receptor simulators or sensors, and/or the like, respectively. Based on the sensor data obtained, the personal tracking device might determine that the user is overdoing a particular physical activity, and might identify one or more user devices (e.g., the user's smart phone, the user's smart watch, tablet computer, mobile phone, television, speaker, other display device, human interface device, etc.) to alert the user of the over-activity, to suggest slowing down, to suggest changing activities to allow the stressed muscles or other portions of the body to recover, to change media content (if user is viewing media content; e.g., from one exercise video focusing on one set of muscle groups to another exercise video focusing on another set of muscle groups, etc.), to direct the user along a different (less strenuous) path if the user is running, roller skating, roller blading, or cycling along a particular strenuous path for a prolonged period, and/or the like.

In another example, the personal tracker 105 might monitor one or more of the heart rate, the blood pressure, the movements of the user, the posture of the user, the blood oxygen level, the blood glucose level, the blood flow level, the nitrogen level, the carbon dioxide level, the sleep patterns, the body temperature, the body fat levels, the body muscle levels, the bone density, the pH, the body fluid content and amount, the brain waves, the synaptic activity, the electroencephalogram, the electrocardiogram, the respiratory rate, the serotonin levels, any signs of epilepsy, the skin toxicity levels, the blood toxicity levels, the organ toxicity levels, any signs of cancer, any signs of pathogens, the content (as well as proportion and amounts) of the user's blood, the blood alcohol level, any presence (and levels) of drugs in the user's body, the level of pain felt by the user, and/or the like, using a heart rate monitor, a blood pressure monitor, accelerometers and/or gyroscopes, one or more location or relative position sensors, an oximeter, a blood glucose monitor, a blood flow monitor, a nitrogen monitor, a carbon dioxide monitor, a sleep monitor, one or more thermometers, one or more body fat monitors, one or more body muscle monitors, one or more bone density monitors, one or more pH monitors, a body fluid monitor, a brain wave monitor, a synaptic activity monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a pathogen detector, a blood tester, one or more blood alcohol level detectors, one or more drug testers, one or more pain receptor simulators or sensors, and/or the like, respectively. Based on the sensor data obtained, the personal tracking device might determine the user's physiological conditions and/or whether the user is in or entering a state of medical emergency, and might identify one or more user devices (e.g., the user's smart phone, the user's smart watch, tablet computer, mobile phone, television, speaker, other display device, human interface device, etc.) that are associated with the user's healthcare provider (e.g., doctor, physician, nurse, caretaker, hospital, HMO, etc.) to alert the healthcare provider of the user's physiological state and/or of the user being in or entering the state of medical emergency. In some cases, the personal tracking device might summon an ambulance (and might provide the location of the user as well as the state or condition of the user to the emergency responders, in some cases, directly to the user devices associated with the emergency responders or the ambulance), and/or the like. In non-emergency situations, the user's doctor (and thus the user) might be provided with long-term monitoring of the physiological and/or environmental conditions of the user, which might help the doctor diagnose conditions that the user might be experiencing or suffering from, and might lead to a cure or to mitigating activities/drugs that can help the user with the conditions.

In yet another example, the personal tracker 105 might monitor at least one of ambient temperature, presence of flame, presence of smoke, presence of other particulates, light levels, humidity/moisture levels, air quality, oxygen level, carbon dioxide level, nitrogen level, atmospheric pressure, carbon monoxide level, presence of gas contaminants or toxins, presence of carcinogens, radiation levels, seismic activity levels, and/or the like, using an ambient temperature sensor, a flame detector, a smoke detector, a particulate sensor, a light sensor, a humidity sensor, an air quality sensor, an atmospheric oxygen level monitor, an atmospheric carbon dioxide level monitor, an atmospheric pressure sensor, an atmospheric nitrogen level monitor, an environmental carbon monoxide sensor, a gas toxicity monitor, a carcinogen detector, a radiation sensor, a seismic sensor, and/or the like, respectively. Based on the sensor data obtained, the personal tracking device might determine that a user (e.g., a miner, a volcanologist, a nuclear facility operator, a nuclear clean-up crew member, a submersible crew member, mountain climbers, canyoneers, cavers, and/or the like) might be in or might be entering an unsafe area, and might identify one or more devices (e.g., the user's smart phone, tablet computer, mobile phone, etc.) that are associated with the user. The activity/fitness tracking and/or medical sensors/monitors (as described above with respect to the exercising user and/or the patient) might similarly be used by the personal tracking device for these users. The sensor data from the combination of physiological and environmental sensors might be used by the personal tracking device to provide the user with guidance as to whether or not to stay in a particular location, to move to some place at least a bit safer, to navigate out of the dangerous environment, to alert outside rescue/response teams as to the location of the user, the physiological condition of the user, and/or the environmental conditions that the user is experience, and/or the like. In some cases, such as in a mine or in a nuclear facility of the like, the personal tracking device might summon lifts, elevators, cars, carts, etc. and/or might request that particular doors be opened to allow the user to pass, and/or the like. The personal tracking device might also communicate with the personal tracking devices of other users in the area to coordinate escape paths or strategies, to consolidate diminishing resources, to coordinate skill sets (e.g., paramedics, doctors, electricians, mechanics, nuclear specialists, climbing guides, engineers, etc.) by the various users, to improve morale, and/or the like.

In a similar manner, other users, including, but not limited to, astronauts, test pilots, emergency responders, deep sea explorers, oil rig workers, construction workers, military combatants, law enforcement officers, peacekeepers, and/or the like, might benefit from use of personal tracking devices that monitor the physiological conditions of each user and/or the environmental conditions experienced by each user, and autonomously interacts with other devices, via machine-to-machine communications, to aid the users, to facilitate work by the user, to help the user survive, to aid other users, to respond to a developing situation or emergency, and/or the like.

Merely by way of example, in some embodiments, the personal tracking device, which might be worn by, and/or implanted in the body, of a child or minor might provide parental notifications, not only concerning accidents or situations involving police, but also if the minor was in danger (e.g., from falling, from being lost, from consuming alcohol, from consuming drugs, from being in dangerous locations (e.g., areas where the minor might fall or hurt himself or herself, areas with reported or detected gun shots, areas in which a natural or manmade disaster is present, areas that lie in the path of a natural or manmade disaster, areas near reported or detected terrorist activities, etc.)), and/or the like. Children's activities and/or medical states/conditions may be monitored in a similar manner as described above with respect to the exercising user and/or the patient, except that the parents of the children might additionally be notified or kept apprised of the children's physiological states/conditions and/or environmental states/conditions.

According to some embodiments, location and/or object identifier beacons might be disposed at potentially dangerous locations (e.g., construction sites, demolition sites, police/FBI investigation sites, potential/actual terrorist sites, actual/predicted disaster zones, and/or the like). Such beacons might announce or broadcast to all compatible devices (including the IoT personal tracking devices of users or the like) warnings regarding the particular location and/or objects within such locations, and the IoT personal tracking devices might utilize such information in determining courses of action to take (e.g., steering the user away from such locations, sending notifications/warnings to the user, etc.) in order to ensure the safety of the user.

In another aspect, the various embodiments might utilize sense and respond IoT devices. For example, a sensor might be used to monitor and report on brain activity and/or synaptic activity throughout the body (such as brainwaves, synaptic activity, etc.). In some cases, the sensor or other implantable devices might have functionality to stimulate nerves, muscles, or the like. Such sensors in conjunction with other body sensors might transmit the sensed data to a database. A processing unit (e.g., computing system 130 or analytics engine 150, or the like) might then query the database and might correlate the received data from the multiple sensors (with pre-analyzed data) to determine activity patterns. Such patterns might correspond to associating particular patterns in the brain to functions performed by the body, by the limbs, by organs, by the mouth, by the ears, etc. The process of correlation might enable the system to learn how a person is able to control his or her body through thoughts including, but not limited to, being able to recognize through patterns associated with communications by monitoring the brain. The IoT sensors may also have embedded within them electrical and/or chemical stimuli-generators that can be used to stimulate nerves, muscles, or other bodily functions. Once the system has learned the brain patterns for an individual, portions of the body can be externally controlled thus enabling a person who becomes physically impaired to someday be able to use the system of the sensors, stimulators, and processors to perform functions that have been interrupted or disconnected due to injury to the brain or to the spinal cord. (Of course, security and encryption would have to be advanced enough to prevent third parties from hijacking the user's bodily functions by hacking into the external control functionalities.) Ultimately, the IoT system might become more than a sensing network, and might become a sense and respond network.

Various other uses or implementations may be made to the various embodiments and examples without departing from the scope of the invention. For example, while the embodiments described above refer to particular features or particular uses, the scope of this invention also includes embodiments having different combination of features or uses, and the embodiments that do not include all of the above described features.

Figure 2A:
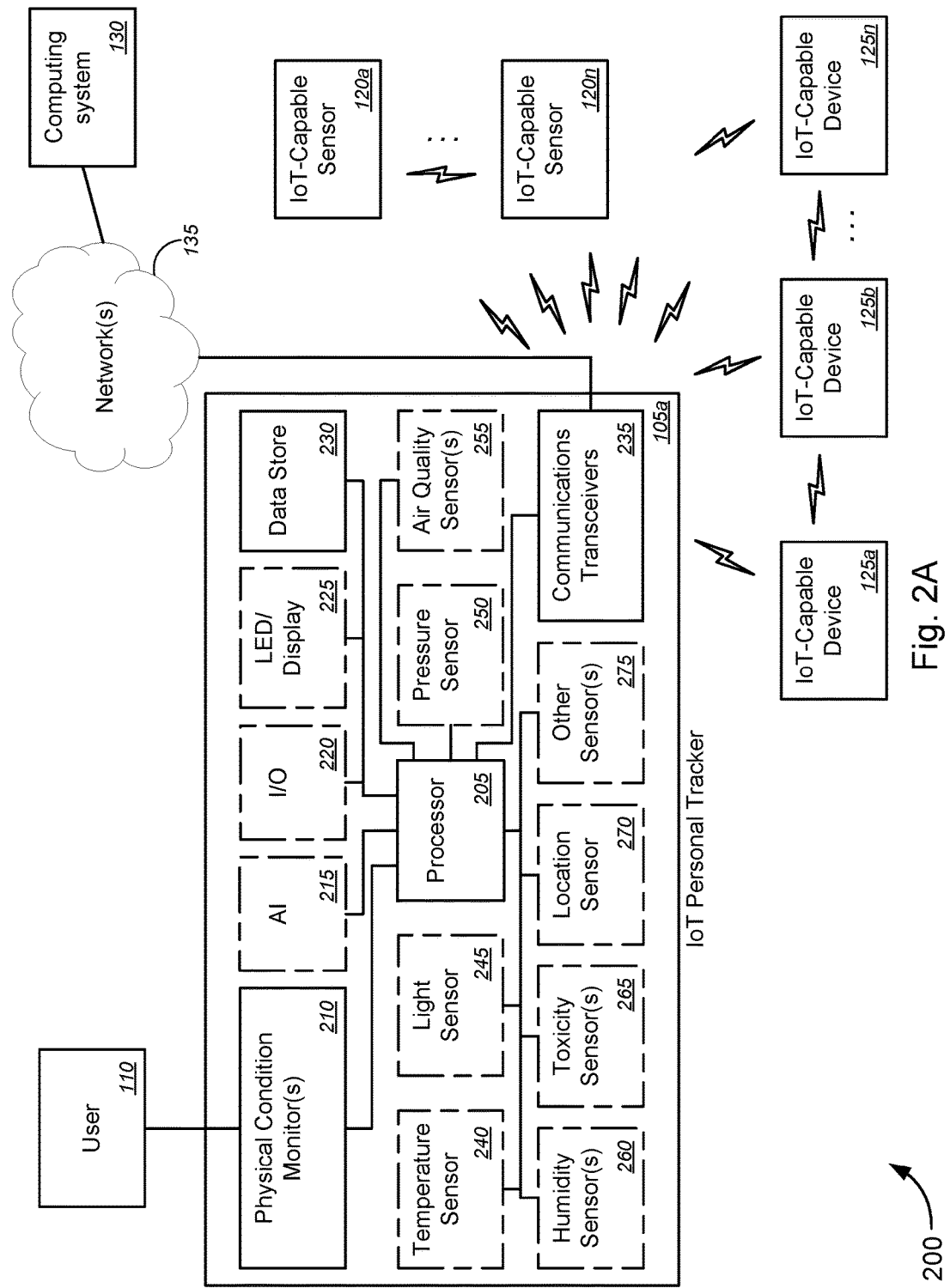
FIGS. 2A-2C are schematic diagrams illustrating various systems for implementing IoT personal tracking functionality, in accordance with various embodiments.
Figure 2B:
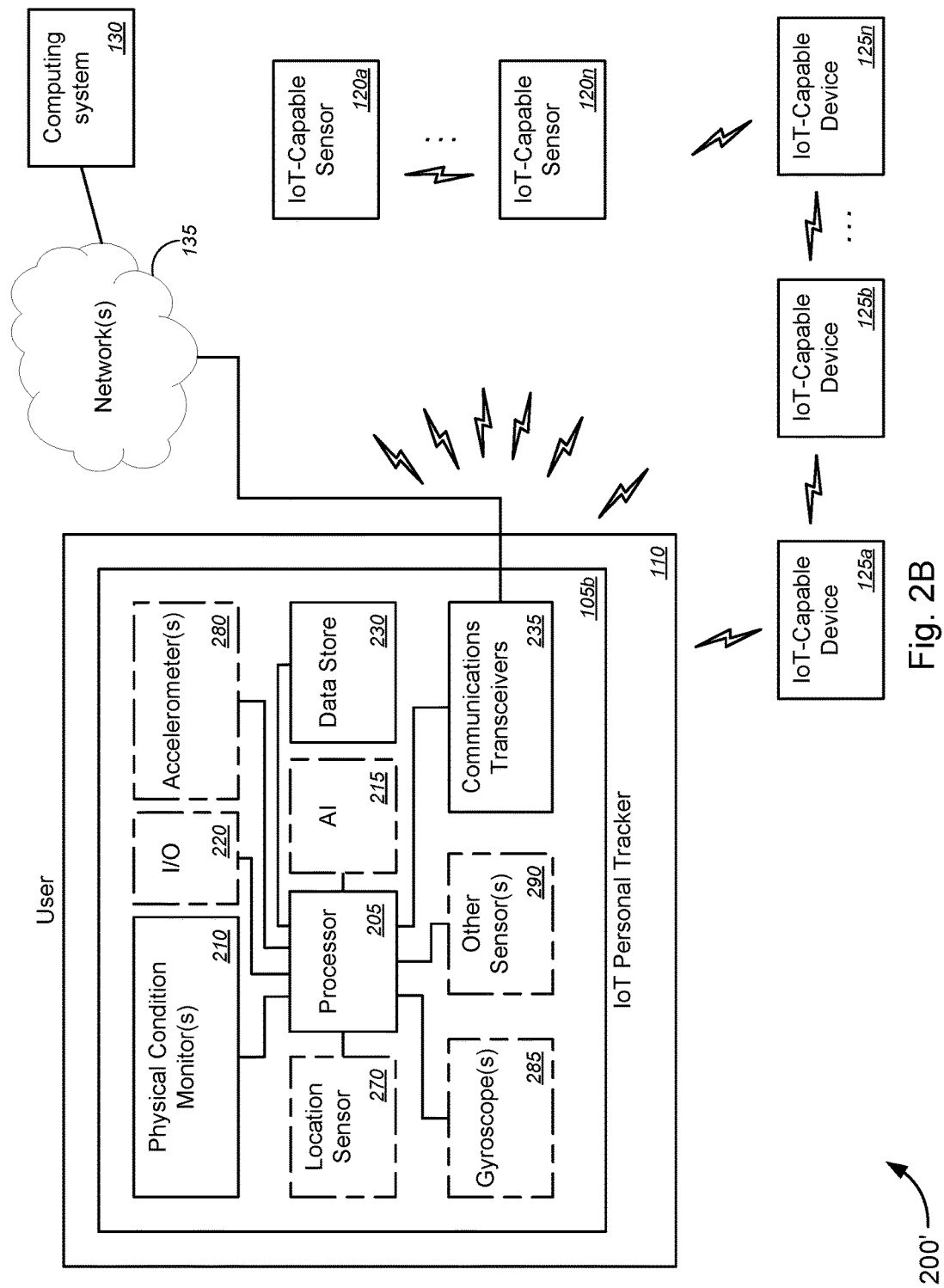
Figure 2C:
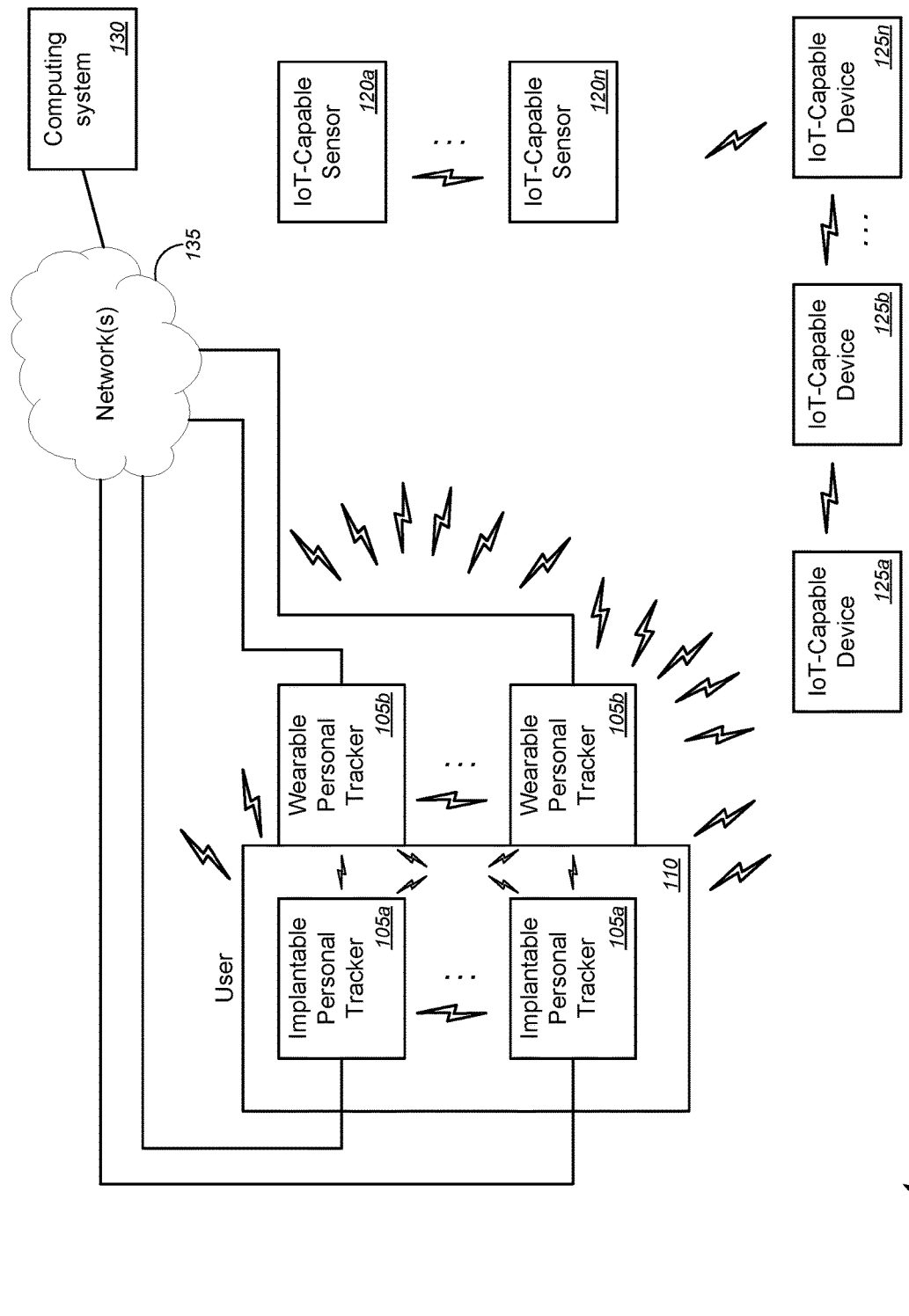

FIGS. 2A-2C (collectively, "FIG. 2") are schematic diagrams illustrating various systems 200, 200', and 200" for implementing IoT personal tracking functionality, in accordance with various embodiments. FIG. 2A depicts an embodiment directed to a wearable personal tracker, while FIG. 2B depicts an embodiment directed to an implantable personal tracker, and FIG. 2C depicts an embodiment directed to a plurality of wearable personal trackers, a plurality of implantable personal trackers, or a combination of at least one wearable personal tracker and at least one implantable personal tracker.

With reference to the non-limiting embodiment of FIG. 2A, according to some embodiments, system 200 might comprise a IoT personal tracking device 105a (which in this case is a wearable personal tracker or at least one that is external to the body of the user) that might include, without limitation, one or more processors 205 (which in some cases might include an artificial intelligence ("AI") system or module 215 (optional)), one or more physical or physiological condition monitors 210, an input/output ("I/O") device 220 (optional), one or more LED/display devices 225 (optional), one or more data stores or computer readable storage media 230, one or more communications transceivers 235, one or more temperature sensors 240 (e.g., heat sensors, infrared sensors, thermometers, ambient temperature sensors, skin temperature sensors, etc.) (optional), one or more light sensors 245 (e.g., ambient light sensors, luminosity sensors, illuminance sensors, solar light sensors, etc.) (optional), one or more pressure sensors 250 (e.g., atmospheric pressure sensors, water pressure sensors (when underwater), etc.) (optional), one or more air quality sensors 255 (e.g., CO sensors, toxic gas sensors, pollution sensors, etc.) (optional), one or more humidity sensors 260 (optional), one or more toxicity sensors 265 (e.g., skin toxicity monitors, gas toxicity monitors, liquid toxicity monitors, poison detectors, carcinogen detectors, etc.) (optional), one or more location sensors 270 (e.g., global positioning system ("GPS") devices, global navigation satellite system ("GNSS") devices, relative position sensors, other location sensors, etc.) (optional), one or more other sensors 275 (optional), and/or the like. In some instances, the one or more other sensors 275 might include, but are not limited to, a flame detector, a particulate sensor, an atmospheric oxygen level monitor, an atmospheric carbon dioxide level monitor, an atmospheric nitrogen level monitor, a smoke detector, a radiation sensor, a telecommunications signal sensor, a sound amplitude sensor, a frequency sensor, one or more accelerometers (e.g., for fitness tracking, fall detection, etc.), one or more proximity sensors (e.g., for sensing proximity to user devices, to IoT-devices, to emergency response devices, to safe zone transponders, to other locations, etc.), a location beacon (that broadcasts or otherwise transmits location information of the object within which the beacon is disposed), an object identifier beacon (that broadcasts or otherwise transmits object identification or identifier information to requesting devices or the like), a weather sensor, or a seismic sensor, and/or the like.

The I/O device 220, in some cases, might include, without limitation, at least one of the following sets of components: a combination of one or more microphones, one or more speakers (which might be built-in speakers or external speakers connected through an audio jack or the like), one or more audio processors, and/or the like for voice interface functionality; one or more of at least one button, at least one touchscreen user interface, at least one display interface, and/or the like for touch interface functionality; one or more vibration, pressure, or force transducers and/or one or more pressure sensors that enable haptic feedback interface functionality; one or more wireless transceivers that communicate with one or more user devices associated with the user using any one or a combination of the wireless protocols described herein (including, but not limited to, 2.4 GHz or 5 GHz WiFi, Bluetooth, Z-wave, ZigBee, etc.) for wireless communication interface functionality; and/or the like. In some cases, the communications transceivers 235 might provide communications (either wired or wireless) between the IoT personal tracking device 105a and the computing system 130 via network(s) 135, might provide machine-to-machine communications (either wired or wireless) between the IoT personal tracking device 105a and each of the IoT-capable sensors 115 and/or 120, might provide machine-to-machine communications (either wired or wireless) between the IoT personal tracking device 105a and each of the IoT-capable devices 125, and/or the like.

In some embodiments, the user might speak with the personal tracking device 105a to set particular modes, to provide information to the personal tracker, to provide commands to the personal tracker, to receive alerts as to the physiological condition or state of the user and/or as to the environmental conditions around the user, to receive suggestions as to courses of action to take in response to sensor data, to receive notifications as to what devices the personal tracker is communicating with (or is about to communicate with) and as to what actions are being performed (or will be performed) as well as updates to the situation, and/or the like. Alternatively, or additionally, the user might interact with the personal tracking device 105a via one or more of at least one button, at least one touchscreen user interface, at least one display interface to perform one or more of these functions. In another alternative or additional embodiment, the user might interact with the personal tracking device 105a via haptic feedback interface, with one or more vibration, pressure, or force transducers providing haptic feedback to the user as a means of provide the user with the alerts, suggestions, notifications, and updates, while one or more pressure sensors might sense (and interpret) the user's response, commands, etc. In yet another alternative or additional embodiment, the user might interact with the personal tracking device 105a via one or more user devices (including, but not limited to, a tablet computer, a smart phone, a mobile phone, a personal digital assistant, a desktop computer, a television, a set-top box, a gaming console, a portable gaming device, a human interface device (such as the IoT human interface device as described in detail in the '028400US and '710 applications, which have already been incorporated herein by reference in their entirety), and/or the like) that are associated with the user and that are in wireless communication with the personal tracking device 105a.

The IoT personal tracker 105a, the user 110, the IoT-capable sensors 115 and/or 120, the IoT-capable devices 125, the computing system 130, and the network 135 of system 200 in FIG. 2A are otherwise similar, if not identical, to the IoT personal tracker 105, the users 110, the IoT-capable sensors 115 and/or 120, the IoT-capable devices 125, the computing system 130, and the network 135, respectively, of system 100 in FIG. 1, and the descriptions of these components of system 100 are applicable to the corresponding components of system 200, respectively.

Turning to FIG. 2B, system 200' might be similar, if not identical, to system 200 of FIG. 2A, except that the IoT personal tracker 105b of system 200' is an implantable personal tracker rather than a wearable personal tracker. Accordingly, the personal tracker 105b of system 200' might include components that are more suited to being implanted within the human body (or animal body in some cases) and might exclude components that are not suited to being implanted within a body. For instance, with reference to FIG. 2B, the personal tracker 105b of system 200' might include, without limitation, one or more processors 205 (which in some cases might include an artificial intelligence ("AI") system or module 215 (optional)), one or more physical or physiological condition monitors 210, an input/output ("I/O") device 220 (optional), one or more data stores or computer readable storage media 230, one or more communications transceivers 235, one or more location sensors 270 (e.g., global positioning system ("GPS") devices, global navigation satellite system ("GNSS") devices, relative position sensors, other location sensors, etc.) (optional), one or more accelerometers 280, one or more gyroscopes 285, one or more other sensors 290 (optional), and/or the like. There would be no need for any of the one or more LED/display devices 225, one or more (external) temperature sensors 240 (e.g., heat sensors, infrared sensors, thermometers, ambient temperature sensors, skin temperature sensors, etc.), one or more light sensors 245 (e.g., ambient light sensors, luminosity sensors, illuminance sensors, solar light sensors, etc.), one or more (external) pressure sensors 250 (e.g., atmospheric pressure sensors, water pressure sensors (when underwater), etc.), one or more air quality sensors 255 (e.g., CO sensors, toxic gas sensors, pollution sensors, etc.), one or more humidity sensors 260, one or more (external) toxicity sensors 265 (e.g., skin toxicity monitors, gas toxicity monitors, liquid toxicity monitors, poison detectors, carcinogen detectors, etc.), and so on. In some instances, the one or more other sensors 290 might include, but are not limited to, a radiation sensor, a telecommunications signal sensor, a sound amplitude sensor, a frequency sensor, one or more proximity sensors (e.g., for sensing proximity to user devices, to IoT-devices, to emergency response devices, to safe zone transponders, to other locations, etc.), a location beacon, an object identifier beacon, and/or the like.

The I/O device 220 of system 200', in some cases, might include, without limitation, at least one of the following sets of components: a combination of one or more microphones, one or more speakers (which might be built-in speakers or external speakers connected through an audio jack or the like), one or more audio processors, and/or the like for voice interface functionality; one or more sets of accelerometers, gyroscopes, location sensors, a location beacon, an object identifier beacon, and/or the like that might be implanted in limbs or appendages (e.g., fingers, hands, forearms, toes, feet, legs, head, etc.) to record particular motions or gestures that can be designated as command gestures for gesture interface functionality; one or more vibration, pressure, or force transducers and/or one or more pressure sensors that enable haptic feedback interface functionality; one or more of electrical synaptic signal simulation generators, electrical synapse monitors, chemical synaptic signal simulation generators, chemical synapse monitors, and/or the like for electrical/chemical or synaptic-simulation interface functionality; one or more wireless transceivers that communicate with one or more user devices associated with the user using any one or a combination of the wireless protocols described herein (including, but not limited to, 2.4 GHz or 5 GHz WiFi, Bluetooth, Z-wave, ZigBee, etc.) for wireless communication interface functionality; and/or the like.

In some cases, the communications transceivers 235 might provide communications (either wired or wireless) between the IoT personal tracking device 105b and the computing system 130 via network(s) 135, might provide machine-to-machine communications (either wired or wireless) between the IoT personal tracking device 105b and each of the IoT-capable sensors 115 and/or 120, might provide machine-to-machine communications (either wired or wireless) between the IoT personal tracking device 105b and each of the IoT-capable devices 125, and/or the like. A non-limiting example of machine-to-machine communications might include machine-to-machine communications between the IoT personal tracking device 105b and an IoT-capable/enabled vehicle such that an alcohol-impaired (or drug-impaired) person would be prevented from driving the vehicle if the physical condition monitors 205 of the IoT personal tracking device 105b detect that the person is under the influence of alcohol (or other drugs). Alternatively, in the case of a self-driving vehicle, the self-driving IoT-capable/enabled vehicle might under similar conditions (i.e., in response to machine-to-machine communications with the IoT personal tracking device 105b indicating that the person is under the influence of alcohol (or other drugs), etc.) take over driving functions and autonomously drive the person to a pre-designated location (e.g., the person's home, a clinic (if overly intoxicated), a home of the person's friend or relative, etc.). In a similar manner, if the physical condition monitors 205 of the IoT personal tracking device 105b detect that the person is injured, and communicates such information to the IoT-capable vehicle (or at least information regarding the need to go to a clinic, emergency room, or other healthcare provider facility, etc.), the self-driving vehicle might navigate and drive the person to the medical facility for the person to receive treatment, and the IoT personal tracking device 105b might transmit the person's vital statistics or other physical condition information to the medical staff in advance of arrival. Alternatively, or additionally, the IoT personal tracking device might communicate directly with a nearby wireless transmitting device (such as a mobile phone, a smart phone, or the like) and might initiate a 911 call (or a call to other predetermined number(s) depending on the sensor data) to report an emergency and to transmit the person's vital statistics or other physical condition information, and/or the like.

In some embodiments, the user might speak with the personal tracking device 105b to set particular modes, to provide information to the personal tracker, to provide commands to the personal tracker, to receive alerts as to the physiological condition or state of the user and/or as to the environmental conditions around the user, to receive suggestions as to courses of action to take in response to sensor data, to receive notifications as to what devices the personal tracker is communicating with (or is about to communicate with) and as to what actions are being performed (or will be performed) as well as updates to the situation, and/or the like. Alternatively, or additionally, the user might interact with the personal tracking device 105b via gestures, by, for example, using one or more sets of accelerometers, gyroscopes, location sensors, a location beacon, an object identifier beacon, and/or the like that might be implanted in limbs or appendages (e.g., fingers, hands, forearms, toes, feet, legs, head, etc.) to record particular motions or gestures that can be designated as command gestures. In another alternative or additional embodiment, the user might interact with the personal tracking device 105b via haptic feedback interface, with one or more vibration, pressure, or force transducers providing haptic feedback to the user as a means of provide the user with the alerts, suggestions, notifications, and updates, while one or more pressure sensors might sense (and interpret) the user's response, commands, etc. In yet another alternative or additional embodiment, the user might interact with the personal tracking device 105b via one or more electrical/chemical or synaptic-simulation interfaces, by using one or more of electrical synaptic signal simulation generators, electrical synapse monitors, chemical synaptic signal simulation generators, chemical synapse monitors, and/or the like to communicate with the personal tracking device 105b via synaptic (or pseudo-synaptic) interface. In still another alternative or additional embodiment, the user might interact with the personal tracking device 105b via one or more user devices (including, but not limited to, a tablet computer, a smart phone, a mobile phone, a personal digital assistant, a desktop computer, a television, a set-top box, a gaming console, a portable gaming device, a human interface device (such as the IoT human interface device as described in detail in the '028400US and '710 applications, which have already been incorporated herein by reference in their entirety), and/or the like) that are associated with the user and that are in wireless communication with the personal tracking device 105a.

The IoT personal tracker 105b, the user 110, the IoT-capable sensors 115 and/or 120, the IoT-capable devices 125, the computing system 130, and the network 135 of system 200' in FIG. 2B would otherwise be similar, if not identical, to the IoT personal tracker 105a, the user 110, the IoT-capable sensors 115 and/or 120, the IoT-capable devices 125, the computing system 130, and the network 135 of system 200 in FIG. 2A, respectively, and to the IoT personal tracker 105, the users 110, the IoT-capable sensors 115 and/or 120, the IoT-capable devices 125, the computing system 130, and the network 135, respectively, of system 100 in FIG. 1, respectively, and the descriptions of these components of systems 100 and 200 are applicable to the corresponding components of system 200'.

In the non-limiting embodiment of FIG. 2C, system 200" might be similar, if not identical, to system 200 of FIG. 2A and system 200' of FIG. 2B, except that system 200" either a plurality of wearable personal trackers 105a, a plurality of implantable personal trackers 105b, or a combination of at least one wearable personal tracker 105a and at least one implantable personal tracker 105b. Each wearable personal tracker 105a might be similar, if not identical, to personal tracker 105a of system 200 of FIG. 2A, while each implantable personal tracker 105b might be similar, if not identical, to personal tracker 105b of system 200' of FIG. 2B. In some cases, the communications transceivers 235 of each personal tracker 105a or 105b might further provide wireless communications between the IoT personal tracking device 105a/105b and each of one or more personal tracking devices 105a and/or 105b.

Each IoT personal tracker 105a and each IoT personal tracker 105b of system 200" in FIG. 2C would otherwise be similar, if not identical, to the IoT personal tracker 105 of system 100 of FIG. 1 or personal tracker 105a of system 200 of FIG. 2A and the IoT personal tracker 105 of system 100 of FIG. 1 or personal tracker 105b of system 200' of FIG. 2B, respectively, and the descriptions of these components of systems 100, 200, and 200' are applicable to the corresponding components of system 200". The user 110, the IoT-capable sensors 115 and/or 120, the IoT-capable devices 125, the computing system 130, and the network 135 of system 200" in FIG. 2C would otherwise be similar, if not identical, to the user 110, the IoT-capable sensors 115 and/or 120, the IoT-capable devices 125, the computing system 130, and the network 135, respectively, of system 100 in FIG. 1, of system 200 in FIG. 2A, or of system 200' in FIG. 2B, and the descriptions of these components of systems 100, 200, and 200' are likewise applicable to the corresponding components of system 200".

Figure 3:
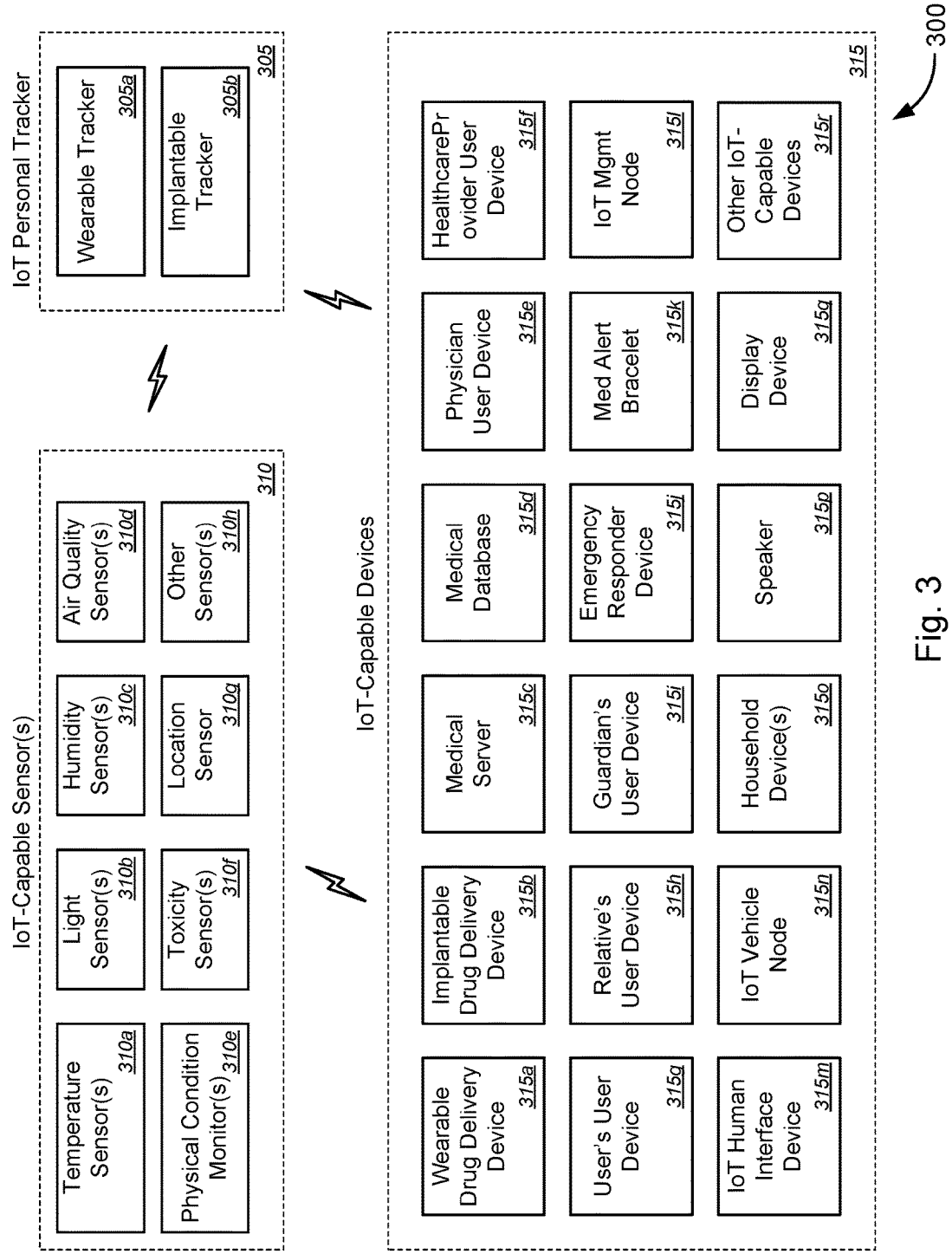
FIG. 3 is a schematic diagram illustrating yet another system for implementing IoT personal tracking functionality, in accordance with various embodiments.

FIG. 3 is a schematic diagram illustrating yet another system 300 for implementing IoT personal tracking functionality, in accordance with various embodiments. In particular, FIG. 3 depicts various examples of IoT-capable sensors 310 and various examples of IoT-capable devices 315 with which the IoT personal tracker or personal tracking device 305 communicates. Some IoT-capable sensors 310, in some cases, also communicate with some IoT-capable devices 315. Although lightning bolt symbols are used to denote wireless communications between two or more of the IoT personal tracker or personal tracking device 305, the IoT-capable sensors 310, and the IoT-capable devices 315, the various embodiments are not so limited, and wired as well as wireless communications may be used. In any event, most communications would be autonomous machine-to-machine communications.

In some embodiments, the IoT personal tracker or personal tracking device 305 might comprise either a wearable tracker 305a or an implantable tracker 305b. As described with respect to FIG. 2C above, multiple personal trackers 305 (whether wearable or implantable) may be implemented in place of or complementary a single personal tracker 305.

According to some embodiments, the IoT-capable sensors 310 might include, without limitation, one or more temperature sensors 310a (e.g., heat sensors, infrared sensors, thermometers, etc.), one or more light sensors 310b (e.g., ambient light sensors, luminosity sensors, illuminance sensors, solar light sensors, etc.), one or more humidity sensors 310c, one or more air quality sensors 310d, one or more physical condition monitors 310e, one or more toxicity sensors 310f (e.g., gas toxicity, liquid toxicity, poison detectors, carcinogen detectors, etc.), one or more location sensors 310g (e.g., global positioning system ("GPS") devices, global navigation satellite system ("GNSS") devices, other location sensors, etc.), one or more other sensors 310h, and/or the like. In some instances, the one or more physical condition monitors 310e might include, without limitation, at least one of a heart rate monitor, a pulse oximeter, an oximeter, a blood glucose monitor, a blood pressure monitor, a blood flow monitor, a nitrogen monitor, a carbon dioxide monitor, a sleep monitor, an activity monitor, a step counter, one or more limb movement monitors, one or more thermometers, one or more accelerometers, one or more gyroscopes, one or more body fat monitors, one or more body muscle monitors, one or more bone density monitors, one or more pH monitors, a body fluid monitor, a brain wave monitor, a synaptic activity monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a pathogen detector, a blood tester, one or more blood alcohol level detectors, one or more drug testers, or one or more location monitors, and/or the like. In some cases, the one or more other sensors 310h might include, but are not limited to, a flame detector, a particulate sensor, an atmospheric oxygen level monitor, an atmospheric carbon dioxide level monitor, an atmospheric nitrogen level monitor, an atmospheric pressure sensor, an environmental carbon monoxide sensor, a smoke detector, a radiation sensor, a telecommunications signal sensor, a sound amplitude sensor, a frequency sensor, a location beacon, an object identifier beacon, or a seismic sensor, and/or the like.

In some embodiments, the IoT-capable devices 315 might include one or more IoT-capable sensors 310 and/or might further include, without limitation, a wearable drug delivery device 315a, an implantable drug delivery device 315b, a medical server 315c, a medical database 315d, a user device associated with a physician 315e, a user device associated with a healthcare provider 315f, a user device associated with the user 315g, a user device associated with a relative of the user 315h, a user device associated with a guardian of the user 315i, a user device associated with an emergency response team member 315j, a smart medical alert bracelet 315k (i.e., a medical alert bracelet that has a digital component that can be updated or the like), an IoT management node 315l, an IoT human interface device 315m (such as an IoT human interface device as described in detail in the '028400US and '710 applications, which have already been incorporated herein by reference in their entirety), an IoT vehicle node 315n, one or more household devices 315o (including, but not limited to, a thermostat or environmental control system, a kitchen appliance (including, but not limited to, a microwave oven, a refrigerator, an oven, a range, a stove, an induction cooktop, a pressure cooker, a rice cooker, a bread maker, a coffee machine, a kettle, a dishwasher, a food thermometer, and/or the like), a medical device, a telephone system, a speaker, a media recording and/or playback device, a lighting system, a customer premises security control system, one or more dedicated remote control devices, one or more universal remote control devices, and/or the like), a speaker 315p, a display device 315q, and/or other IoT-capable devices 315r. In some cases, the other IoT-capable devices 315r might include, without limitation, a personal digital assistant, a printer, a scanner, an image projection device, a video projection device, a household appliance, a vehicle, an audio headset, earbuds, virtual reality goggles or headset, augmented reality goggles or headset, a door locking system, an automated door opening/closing system, a window locking system, an automated window opening or closing system, a window covering control system, a smart window, a solar cell or solar cell array, an electrical outlet or smart node, a power strip or bar, a dimmer switch, a data port, a sprinkler system, exercise equipment, one or more office devices, one or more lighting systems, one or more communications systems, a user device associated with a member of an organization with which the user is affiliated (e.g., a club, a school, a company/employer, a prison, a rewards club, etc.), and/or the like. In some cases, each of the user device associated with a physician 315e, the user device associated with a healthcare provider 315*f*, the user device associated with the user 315*g*, the user device associated with a relative of the user 315*h*, the user device associated with a guardian of the user 315*i*, the user device associated with an emergency response team member 315*j*, and the user device associated with a member of an organization with which the user is affiliated might comprise at least one of a desktop computer, a laptop computer, a tablet computer, a smart phone, a mobile phone, a portable gaming device, a television or monitor, a set-top box ("STB"), a gaming console, an image capture device, a video capture device, and/or the like.

The IoT personal tracker or personal tracking device 305, the IoT-capable sensors 310, and the IoT-capable devices 315 are otherwise similar, if not identical, to the IoT personal tracker or personal tracking device 105, the IoT-capable sensors 115 or 120, and the IoT-capable devices 125, respectively, as described above with respect to FIGS. 1 and 2.

Figure 4A:
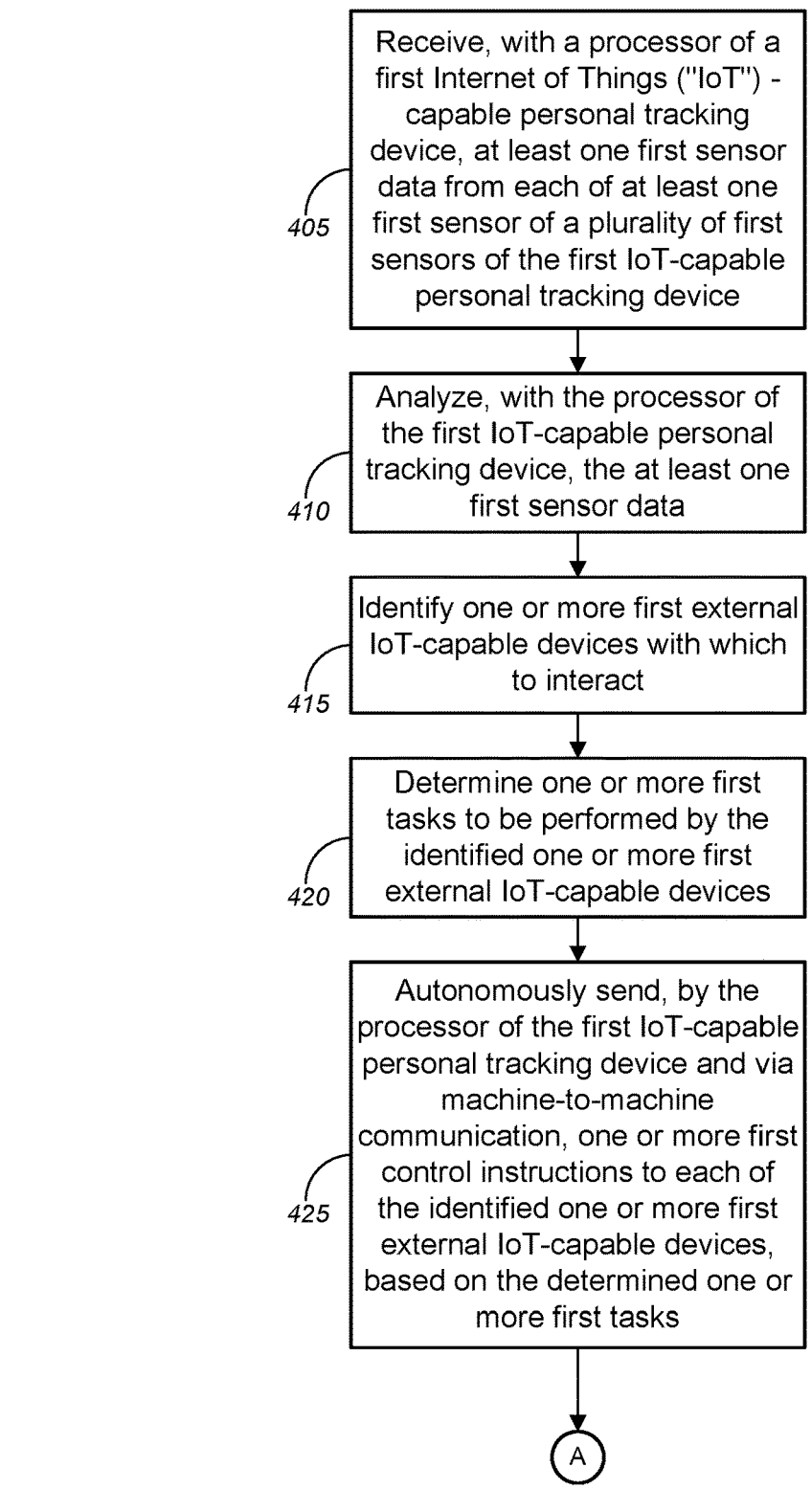
FIGS. 4A and 4B are flow diagrams illustrating a method for implementing IoT personal tracking functionality, in accordance with various embodiments.
Figure 4B:
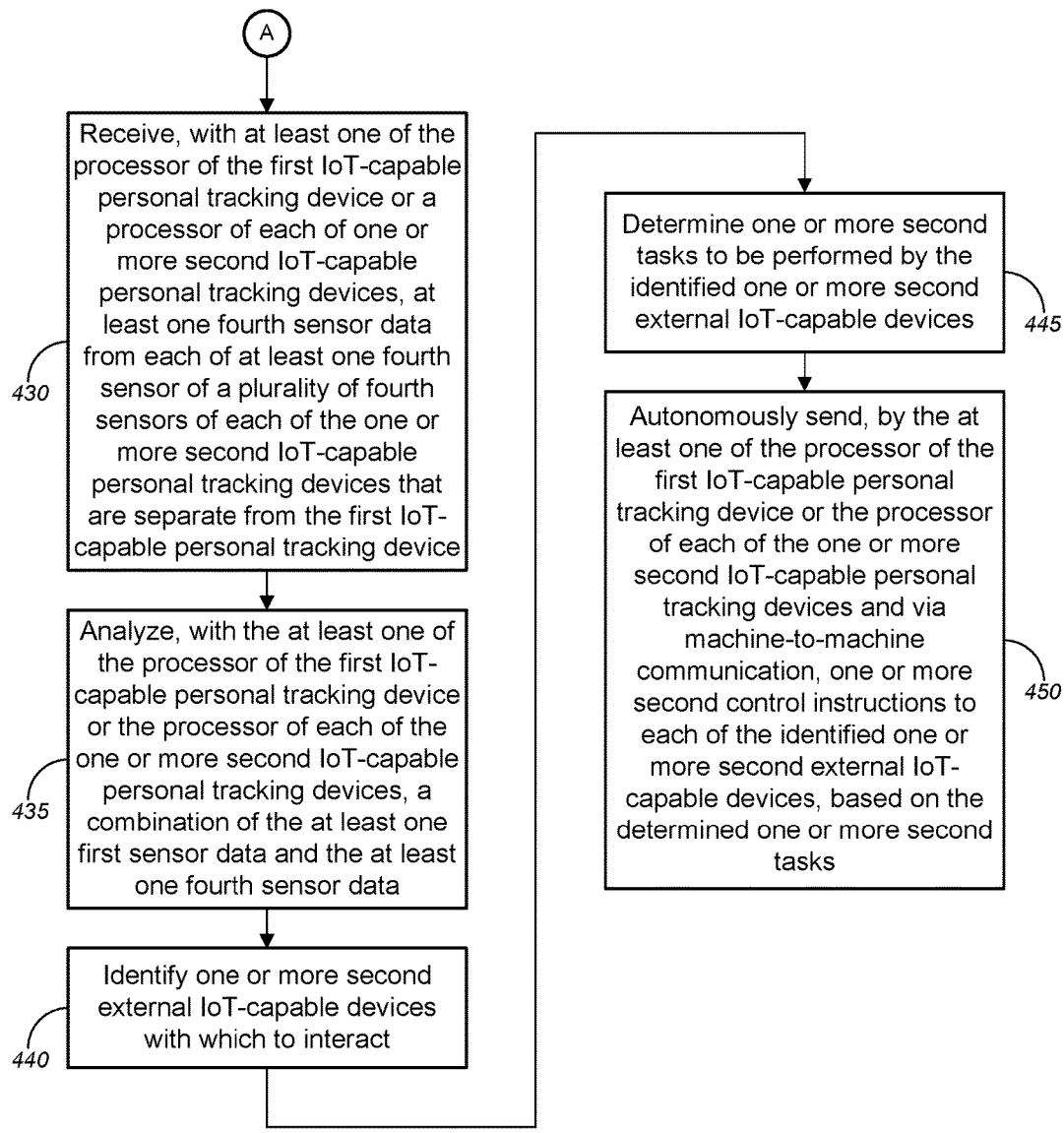

FIGS. 4A and 4B (collectively, "FIG. 4") are flow diagrams illustrating a method 400 for implementing IoT personal tracking functionality, in accordance with various embodiments. While the techniques and procedures are depicted and/or described in a certain order for purposes of illustration, it should be appreciated that certain procedures may be reordered and/or omitted within the scope of various embodiments. Moreover, while the method 400 illustrated by FIG. 4 can be implemented by or with (and, in some cases, are described below with respect to) the systems 100, 200, 200', 200", and 300 of FIGS. 1, 2A, 2B, 2C, and 3 respectively (or components thereof), such methods may also be implemented using any suitable hardware (or software) implementation. Similarly, while each of the systems 100, 200, 200', 200", and 300 of FIGS. 1, 2A, 2B, 2C, and 3, respectively (or components thereof), can operate according to the method 400 illustrated by FIG. 4 (e.g., by executing instructions embodied on a computer readable medium), the systems 100, 200, 200', 200", and 300 of FIGS. 1, 2A, 2B, 2C, and 3 can each also operate according to other modes of operation and/or perform other suitable procedures.

In FIG. 4A, method 400, at block 405, might comprise receiving, with a processor of a first Internet of Things ("IoT")-capable personal tracking device (which might correspond to IoT-capable personal tracking device 105, 105*a*, 105*b*, 305, 305*a*, and 305*b* of FIGS. 1-3, or the like), at least one first sensor data from each of at least one first sensor of a plurality of first sensors (which might correspond to Built-In IoT-capable sensors 115*a*-115*n*, 205, 240-290, 310, and 310*a*-310*h*, External IoT-capable sensors 120*a*-120*n*, 310, and 310*a*-310*h* of FIGS. 1-3, or the like) of the first IoT-capable personal tracking device. The plurality of first sensors might comprise at least one of one or more second sensors that monitor physical conditions of a body of a user or one or more third sensors that monitor environmental conditions external to the body of the user. In some embodiments, the first IoT-capable personal tracking device might be a wearable device, which might include, without limitation, at least one of a wrist strap, a clip, a pin, a clasp, an ear-loop, a finger ring, a toe ring, a bangle, a hook and loop-type strap, eyewear stems, a head band, or a buckle, and/or the like that allows the first IoT-capable personal tracking device to be removably affixed to at least one of a portion of skin of the user, a limb of the user, an appendage of the user, a torso of the user, a head of the user, or a piece of clothing worn by the user, and/or the like. Alternatively, the first IoT-capable personal tracking device might be an implantable device, which might include, but is not limited to, at least one of an encapsulation layer, a membrane, a hypo-allergenic housing, a capsule, or casing, and/or the like that allows the first IoT-capable personal tracking device to be at least one of implanted under one or more layers of skin of the user, implanted within an organ of the user, implanted within a torso of the user, implanted within a head of the user, implanted within a spine of the user, implanted in an internal cavity of the user, or implanted in an external cavity of the user, and/or the like.

According to some embodiments, the one or more second sensors might include, without limitation, at least one of a heart rate monitor, a pulse oximeter, an oximeter, a blood glucose monitor, a blood pressure monitor, a blood flow monitor, a nitrogen monitor, a carbon dioxide monitor, a sleep monitor, an activity monitor, a step counter, one or more limb movement monitors, one or more thermometers, one or more accelerometers, one or more gyroscopes, one or more body fat monitors, one or more body muscle monitors, one or more bone density monitors, one or more pH monitors, a body fluid monitor, a brain wave monitor, a synaptic activity monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a pathogen detector, a blood tester, one or more blood alcohol level detectors, one or more drug testers, or one or more location monitors, and/or the like. In some instances, the one or more third sensors comprise at least one of an ambient temperature sensor, a flame detector, a particulate sensor, a light sensor, a humidity sensor, an air quality sensor, an atmospheric oxygen level monitor, an atmospheric carbon dioxide level monitor, an atmospheric nitrogen level monitor, an atmospheric pressure sensor, an environmental carbon monoxide sensor, a smoke detector, a gas toxicity monitor, a carcinogen detector, a radiation sensor, a location sensor, a location beacon, an object identifier beacon, a telecommunications signal sensor, a sound amplitude sensor, a frequency sensor, or a seismic sensor, and/or the like.

At block 410, method 400 might comprise analyzing, with the processor of the first IoT-capable personal tracking device, the at least one first sensor data to identify one or more first external IoT-capable devices with which to interact (block 415) and to determine one or more first tasks to be performed by the identified one or more first external IoT-capable devices (block 415), each based at least in part on the at least one first sensor data from each of the at least one first sensor. In some embodiments, the analysis at block 410 might be augmented or entirely performed by at least one of a remote computing system or an analytics engine (and corresponding databases) (which might correspond to computing system 130 or analytics engine 150 (and corresponding databases 145 and 155) of system 100 or the like).

Method 400 might further comprise autonomously sending, by the processor of the first IoT-capable personal tracking device and via machine-to-machine communication, one or more first control instructions to each of the identified one or more first external IoT-capable devices, based on the determined one or more first tasks (block 425). In some embodiments, the one or more first external IoT-capable devices (which might correspond to IoT-capable devices 125*a*-125*n*, 315, and 315*a*-315*r* of FIGS. 1-3, or the like) might include, but are not limited to, at least one of a wearable drug delivery device, an implantable drug delivery device, a medical server, a medical database, a user device associated with a physician, a user device associated with a healthcare provider, a user device associated with the user, a user device associated with a relative or guardian of the user, a user device associated with a member of an organization with which the user is affiliated (e.g., a club, a school, a company/employer, a prison, a rewards club, etc.), a user device associated with an emergency response team member, a smart medical alert bracelet, an IoT management node, an IoT human interface device, an IoT vehicle node, one or more household devices, one or more office devices, one or more lighting systems, one or more environmental control systems, one or more speakers, one or more display devices, or one or more communications systems, and/or the like. The process then proceeds to block 430 in FIG. 4B, following the circular marker denoted, "A."

With reference to FIG. 4B, method 400, at block 430, might comprise receiving, with at least one of the processor of the first IoT-capable personal tracking device or a processor of each of one or more second IoT-capable personal tracking devices, at least one fourth sensor data from each of at least one fourth sensor of a plurality of fourth sensors of each of the one or more second IoT-capable personal tracking devices, the one or more second IoT-capable personal tracking devices being are separate from the first IoT-capable personal tracking device. The plurality of fourth sensors might comprise at least one of one or more fifth sensors that monitor physical conditions of the body of the user or one or more sixth sensors that monitor environmental conditions external to the body of the user. In some embodiments, each of the one or more second IoT-capable personal tracking devices might be similar, if not identical, in terms of structure, form factor, and/or functionality, etc. to the first IoT-capable personal tracking device. Likewise, the one or more fifth sensors and the one or more sixth sensors might be similar, if not identical, in terms of structure, form factor, and/or functionality, etc. to the one or more second sensors and the one or more third sensors, respectively.

At block 435, method 400 might comprise analyzing, with the at least one of the processor of the first IoT-capable personal tracking device or the processor of each of the one or more second IoT-capable personal tracking devices, a combination of the at least one first sensor data and the at least one fourth sensor data to identify one or more second external IoT-capable devices with which to interact (block 440) and to determine one or more second tasks to be performed by the identified one or more second external IoT-capable devices (block 445), each based at least in part on the at least one first sensor data from the at least one first sensor of the first IoT-capable personal tracking device and the at least one fourth sensor data from each of the at least one fourth sensor of each of the one or more second IoT-capable personal tracking devices Method 400 might further comprise autonomously sending, by the at least one of the processor of the first IoT-capable personal tracking device or the processor of each of the one or more second IoT-capable personal tracking devices and via machine-to-machine communication, one or more second control instructions to each of the identified one or more second external IoT-capable devices, based on the determined one or more second tasks (block 450). According to some embodiments, the one or more second external IoT-capable devices might be similar, if not identical, in terms of structure, form factor, and/or functionality, etc. to the one or more first external IoT-capable devices. In some instances, at least one of the one or more first external IoT-capable devices and at least one of the one or more second external IoT-capable devices might be the same external IoT-capable device.

According to some embodiments, analyzing, with the processor of the first IoT-capable personal tracking device, the at least one first sensor data might comprise analyzing, with the processor of the first IoT-capable personal tracking device, the at least one first sensor data to identify one or more first external IoT-capable devices with which to interact and to determine one or more first tasks to be performed by the identified one or more first external IoT-capable devices, each based at least in part on the at least one first sensor data from each of the at least one first sensor, utilizing artificial intelligence ("AI") to improve identification of external IoT-capable devices and determination of the one or more first tasks to be performed. The AI may be further utilized to improve machine-to-machine interactions and to improve utilization of the at least one first sensor and the plurality of IoT-capable devices. In a similar manner and to achieve similar results, AI may be used for analyzing sensor data from multiple personal tracking devices rather than from a single personal tracking device.

Exemplary System and Hardware Implementation

Figure 5:
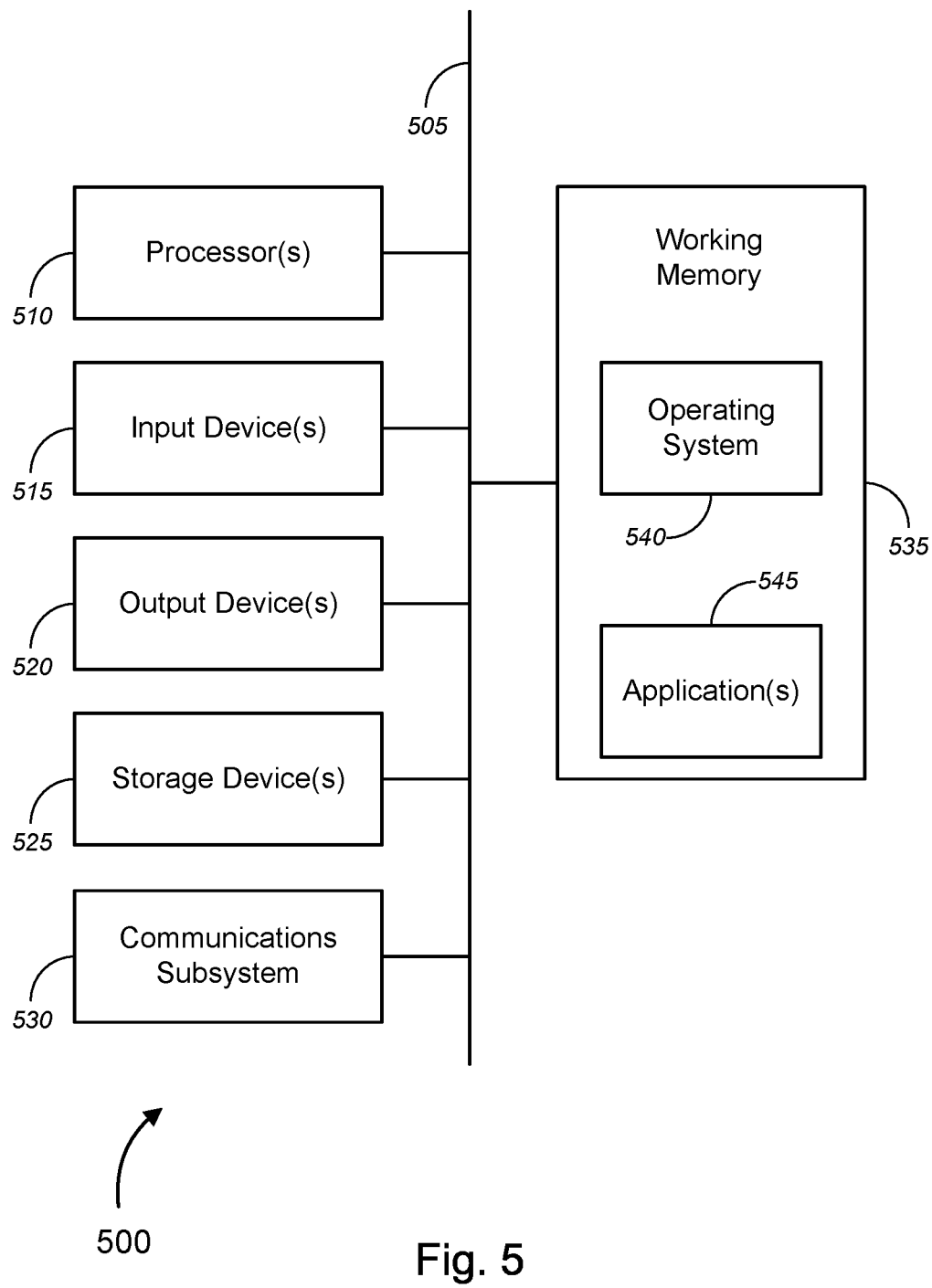
FIG. 5 is a block diagram illustrating an exemplary computer or system hardware architecture, in accordance with various embodiments.

FIG. 5 is a block diagram illustrating an exemplary computer or system hardware architecture, in accordance with various embodiments. FIG. 5 provides a schematic illustration of one embodiment of a computer system 500 of the service provider system hardware that can perform the methods provided by various other embodiments, as described herein, and/or can perform the functions of computer or hardware system (i.e., Internet of Things ("IoT") personal tracking devices 105, 105a, 105b, 305, 305a, and 305b, Built-In IoT-capable sensors 115a-115n, 205, 240-290, 310, and 310a-310h, External IoT-capable sensors 120a-120n, 310, and 310a-310h, IoT-capable devices 125a-125n, 315, and 315a-315r, computing system 130, analytics engine 150, etc.), as described above. It should be noted that FIG. 5 is meant only to provide a generalized illustration of various components, of which one or more (or none) of each may be utilized as appropriate. FIG. 5, therefore, broadly illustrates how individual system elements may be implemented in a relatively separated or relatively more integrated manner.

The computer or hardware system 500—which might represent an embodiment of the computer or hardware system (i.e., IoT personal tracking devices 105, 105a, 105b, 305, 305a, and 305b, Built-In IoT-capable sensors 115a-115n, 205, 240-290, 310, and 310a-310h, External IoT-capable sensors 120a-120n, 310, and 310a-310h, IoT-capable devices 125a-125n, 315, and 315a-315r, computing system 130, analytics engine 150, etc.), described above with respect to FIGS. 1-4—is shown comprising hardware elements that can be electrically coupled via a bus 505 (or may otherwise be in communication, as appropriate). The hardware elements may include one or more processors 510, including, without limitation, one or more general-purpose processors and/or one or more special-purpose processors (such as microprocessors, digital signal processing chips, graphics acceleration processors, and/or the like); one or more input devices 515, which can include, without limitation, a mouse, a keyboard, and/or the like; and one or more output devices 520, which can include, without limitation, a display device, a printer, and/or the like.

The computer or hardware system 500 may further include (and/or be in communication with) one or more storage devices 525, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable, and/or the like. Such storage devices may be configured to implement any appropriate data stores, including, without limitation, various file systems, database structures, and/or the like.

The computer or hardware system 500 might also include a communications subsystem 530, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, a Z-Wave device, a ZigBee device, cellular communication facilities, etc.), and/or the like. The communications subsystem 530 may permit data to be exchanged with a network (such as the network described below, to name one example), with other computer or hardware systems, and/or with any other devices described herein. In many embodiments, the computer or hardware system 500 will further comprise a working memory 535, which can include a RAM or ROM device, as described above.

The computer or hardware system 500 also may comprise software elements, shown as being currently located within the working memory 535, including an operating system 540, device drivers, executable libraries, and/or other code, such as one or more application programs 545, which may comprise computer programs provided by various embodiments (including, without limitation, hypervisors, VMs, and the like), and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 525 described above. In some cases, the storage medium might be incorporated within a computer system, such as the system 500. In other embodiments, the storage medium might be separate from a computer system (i.e., a removable medium, such as a compact disc, etc.), and/or provided in an installation package, such that the storage medium can be used to program, configure, and/or adapt a general purpose computer with the instructions/code stored thereon. These instructions might take the form of executable code, which is executable by the computer or hardware system 500 and/or might take the form of source and/or installable code, which, upon compilation and/or installation on the computer or hardware system 500 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer or hardware system 500) to perform methods in accordance with various embodiments of the invention. According to a set of embodiments, some or all of the procedures of such methods are performed by the computer or hardware system 500 in response to processor 510 executing one or more sequences of one or more instructions (which might be incorporated into the operating system 540 and/or other code, such as an application program 545) contained in the working memory 535. Such instructions may be read into the working memory 535 from another computer readable medium, such as one or more of the storage device(s) 525. Merely by way of example, execution of the sequences of instructions contained in the working memory 535 might cause the processor(s) 510 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 500, various computer readable media might be involved in providing instructions/code to processor(s) 510 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 525. Volatile media includes, without limitation, dynamic memory, such as the working memory 535. In some alternative embodiments, a computer readable medium may take the form of transmission media, which includes, without limitation, coaxial cables, copper wire and fiber optics, including the wires that comprise the bus 505, as well as the various components of the communication subsystem 530 (and/or the media by which the communications subsystem 530 provides communication with other devices). In an alternative set of embodiments, transmission media can also take the form of waves (including, without limitation, radio, acoustic, and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 510 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 500. These signals, which might be in the form of electromagnetic signals, acoustic signals, optical signals, and/or the like, are all examples of carrier waves on which instructions can be encoded, in accordance with various embodiments of the invention.

The communications subsystem 530 (and/or components thereof) generally will receive the signals, and the bus 505 then might carry the signals (and/or the data, instructions, etc. carried by the signals) to the working memory 535, from which the processor(s) 505 retrieves and executes the instructions. The instructions received by the working memory 535 may optionally be stored on a storage device 525 either before or after execution by the processor(s) 510.

Figure 6:
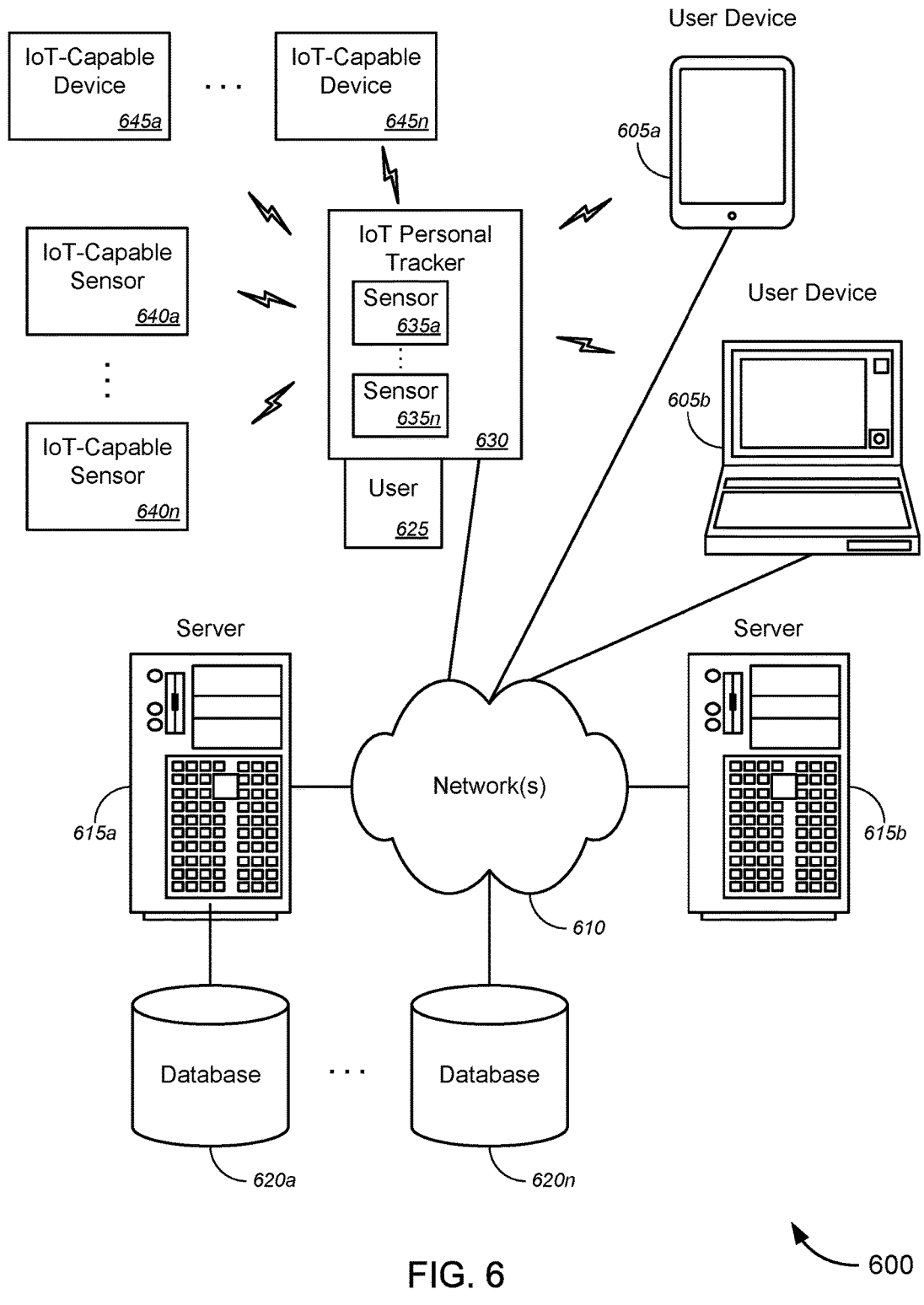
FIG. 6 is a block diagram illustrating an example of a networked system of computers, computing systems, or system hardware architecture, which can be used in accordance with various embodiments.

As noted above, a set of embodiments comprises methods and systems for implementing Internet of Things functionality, and, in particular embodiments, to methods, systems, apparatus, and computer software for implementing Internet of Things ("IoT") personal tracking functionality. FIG. 6 illustrates a schematic diagram of a system 600 that can be used in accordance with various embodiments. The system 600 can each include one or more user computers, user devices, or customer devices 605. A user computer, user device, or customer device 605 can be a general purpose personal computer (including, merely by way of example, desktop computers, tablet computers, laptop computers, handheld computers, and the like, running any appropriate operating system, several of which are available from vendors such as Apple, Microsoft Corp., and the like), cloud computing devices, a server(s), and/or a workstation computer(s) running any of a variety of commercially-available UNIX™ or UNIX-like operating systems. A user computer, user device, or customer device 605 can also have any of a variety of applications, including one or more applications configured to perform methods provided by various embodiments (as described above, for example), as well as one or more office applications, database client and/or server applications, and/or web browser applications. Alternatively, a user computer, user device, or customer device 605 can be any other electronic device, such as a thin-client computer, Internet-enabled mobile telephone, and/or personal digital assistant, capable of communicating via a network (e.g., the network(s) 610 described below) and/or of displaying and navigating web pages or other types of electronic documents. Although the exemplary system 600 is shown with two user computers, user devices, or customer devices 605, any number of user computers, user devices, or customer devices can be supported.

Certain embodiments operate in a networked environment, which can include a network(s) 610. The network(s) 610 can be any type of network familiar to those skilled in the art that can support data communications using any of a variety of commercially-available (and/or free or proprietary) protocols, including, without limitation, TCP/IP, SNA™, IPX™, AppleTalk™, and the like. Merely by way of example, the network(s) 610 (similar to network 130 of FIGS. 1 and 2, or the like) can each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, the Z-Wave protocol known in the art, the ZigBee protocol or other IEEE 802.15.4 suite of protocols known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, and/or the Internet.

Embodiments can also include one or more server computers 615. Each of the server computers 615 may be configured with an operating system, including, without limitation, any of those discussed above, as well as any commercially (or freely) available server operating systems. Each of the servers 615 may also be running one or more applications, which can be configured to provide services to one or more clients 605 and/or other servers 615.

Merely by way of example, one of the servers 615 might be a data server, a web server, a cloud computing device(s), or the like, as described above. The data server might include (or be in communication with) a web server, which can be used, merely by way of example, to process requests for web pages or other electronic documents from user computers 605. The web server can also run a variety of server applications, including HTTP servers, FTP servers, CGI servers, database servers, Java servers, and the like. In some embodiments of the invention, the web server may be configured to serve web pages that can be operated within a web browser on one or more of the user computers 605 to perform methods of the invention.

The server computers 615, in some embodiments, might include one or more application servers, which can be configured with one or more applications accessible by a client running on one or more of the client computers 605 and/or other servers 615. Merely by way of example, the server(s) 615 can be one or more general purpose computers capable of executing programs or scripts in response to the user computers 605 and/or other servers 615, including, without limitation, web applications (which might, in some cases, be configured to perform methods provided by various embodiments). Merely by way of example, a web application can be implemented as one or more scripts or programs written in any suitable programming language, such as Java™, C, C#™ or C++, and/or any scripting language, such as Perl, Python, or TCL, as well as combinations of any programming and/or scripting languages. The application server(s) can also include database servers, including, without limitation, those commercially available from Oracle™, Microsoft™, Sybase™, IBM™, and the like, which can process requests from clients (including, depending on the configuration, dedicated database clients, API clients, web browsers, etc.) running on a user computer, user device, or customer device 605 and/or another server 615. In some embodiments, an application server can perform one or more of the processes for implementing Internet of Things functionality, and, in particular embodiments, to methods, systems, apparatus, and computer software for implementing Internet of Things ("IoT") personal tracking functionality, or the like, as described in detail above. Data provided by an application server may be formatted as one or more web pages (comprising HTML, JavaScript, etc., for example) and/or may be forwarded to a user computer 605 via a web server (as described above, for example). Similarly, a web server might receive web page requests and/or input data from a user computer 605 and/or forward the web page requests and/or input data to an application server. In some cases, a web server may be integrated with an application server.

In accordance with further embodiments, one or more servers 615 can function as a file server and/or can include one or more of the files (e.g., application code, data files, etc.) necessary to implement various disclosed methods, incorporated by an application running on a user computer 605 and/or another server 615. Alternatively, as those skilled in the art will appreciate, a file server can include all necessary files, allowing such an application to be invoked remotely by a user computer, user device, or customer device 605 and/or server 615.

It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 620a-620n (collectively, "databases 620"). The location of each of the databases 620 is discretionary: merely by way of example, a database 620a might reside on a storage medium local to (and/or resident in) a server 615a (and/or a user computer, user device, or customer device 605). Alternatively, a database 620n can be remote from any or all of the computers 605, 615, so long as it can be in communication (e.g., via the network 610) with one or more of these. In a particular set of embodiments, a database 620 can reside in a storage-area network ("SAN") familiar to those skilled in the art. (Likewise, any necessary files for performing the functions attributed to the computers 605, 615 can be stored locally on the respective computer and/or remotely, as appropriate.) In one set of embodiments, the database 620 can be a relational database, such as an Oracle database, that is adapted to store, update, and retrieve data in response to SQL-formatted commands. The database might be controlled and/or maintained by a database server, as described above, for example.

With reference to FIG. 6, according to some embodiments, system 600 might further comprise an IoT personal tracking device 630 (similar to IoT personal tracking device 105, 105a, 105b, 305, 305a, and 305b of FIGS. 1-3, or the like) that is either worn by a user 625 or implanted within the body of the user 625, one or more IoT-capable sensors 635a-635n or 640a-640n (similar to Built-In IoT-capable sensors 115a-115n, 205, 240-290, 310, and 310a-310h, External IoT-capable sensors 120a-120n, 310, and 310a-310h of FIGS. 1-3, or the like), and one or more IoT-capable devices 645a-645n (similar to IoT-capable devices 125a-125n, 315, and 315a-315r of FIGS. 1-3, or the like).

In operation, the IoT personal tracking device 630 might receive at least one sensor data from each of at least one sensor of the one or more IoT-capable sensors 635a-635n or 640a-640n. The personal tracking device 630 might analyze the at least one sensor data to identify at least one IoT-capable device 645 of the one or more IoT-capable devices 645a-645n with which to interact and to determine one or more tasks to be performed by the identified at least one IoT-capable device 645, each based at least in part on the at least one sensor data from each of the at least one sensor. The personal tracking device 630 might subsequently autonomously send, via machine-to-machine communication, one or more control instructions to each of the identified at least one IoT-capable device 645, based on the determined one or more tasks. In some cases, the one or more IoT-capable devices 645a-645n might comprise the user computer, user device, or customer device 605. The machine-to-machine communications between the IoT personal tracking device 630 and each of the user devices 605a or 605b, the IoT-capable sensors 640a-640n, and the IoT-capable devices 645a-645n are represented in FIG. 6 by the lightning bolt symbols, which in some cases denotes wireless communications (although, in some instances, need not be wireless, but can be wired communications). These and other functions of the system 600 (and its components) are described in greater detail above with respect to FIGS. 1-4.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method, comprising:
receiving, with a processor of a first Internet of Things ("IoT") -capable personal tracking device, at least one first sensor data from each of at least one first sensor of a plurality of first sensors of the first IoT-capable personal tracking device, wherein the plurality of first sensors comprises at least one of one or more second sensors that monitor physical conditions of a body of a user or one or more third sensors that monitor environmental conditions external to the body of the user;
analyzing, with the processor of the first IoT-capable personal tracking device, the at least one first sensor data to identify one or more first external IoT-capable devices with which to interact and to determine one or more first tasks to be performed by the identified one or more first external IoT-capable devices, each based at least in part on the at least one first sensor data from each of the at least one first sensor, wherein the one or more first external IoT-capable devices are separate from the personal tracking devices and wherein the one or more first external IoT-capable devices comprise at least one of a wearable drug delivery device, an implantable drug delivery device, a smart medical alert bracelet, an IoT vehicle node, one or more lighting systems, one or more environmental control systems, one or more speakers, or one or more security control systems; and
autonomously sending, by the processor of the first IoT-capable personal tracking device and via machine-to-machine communication, one or more first control instructions to each of the identified one or more first external IoT-capable devices, based on the determined one or more first tasks.

2. The method of claim 1, wherein the first IoT-capable personal tracking device is a wearable device.

3. The method of claim 2, wherein the wearable device comprises at least one of a wrist strap, a clip, a pin, a clasp, an ear-loop, a finger ring, a toe ring, a bangle, a hook and loop-type strap, eyewear stems, a head band, or a buckle that allows the first IoT-capable personal tracking device to be removably affixed to at least one of a portion of skin of the user, a limb of the user, an appendage of the user, a torso of the user, a head of the user, or a piece of clothing worn by the user.

4. The method of claim 1, wherein the first IoT-capable personal tracking device is an implantable device.

5. The method of claim 4, wherein the implantable device comprises at least one of an encapsulation layer, a membrane, a hypo-allergenic housing, a capsule, or casing that allows the first IoT-capable personal tracking device to be at least one of implanted under one or more layers of skin of the user, implanted within an organ of the user, implanted within a torso of the user, implanted within a head of the user, implanted within a spine of the user, implanted in an internal cavity of the user, or implanted in an external cavity of the user.

6. The method of claim 1, wherein the one or more second sensors comprise at least one of a heart rate monitor, a pulse oximeter, an oximeter, a blood glucose monitor, a blood pressure monitor, a blood flow monitor, a nitrogen monitor, a carbon dioxide monitor, a sleep monitor, an activity monitor, a step counter, one or more limb movement monitors, one or more thermometers, one or more accelerometers, one or more gyroscopes, one or more body fat monitors, one or more body muscle monitors, one or more bone density monitors, one or more pH monitors, a body fluid monitor, a brain wave monitor, a synaptic activity monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a pathogen detector, a blood tester, one or more blood alcohol level detectors, one or more drug testers, or one or more location monitors.

7. The method of claim 1, wherein the one or more third sensors comprise at least one of an ambient temperature sensor, a flame detector, a particulate sensor, a light sensor, a humidity sensor, an air quality sensor, an atmospheric oxygen level monitor, an atmospheric carbon dioxide level monitor, an atmospheric nitrogen level monitor, an atmospheric pressure sensor, an environmental carbon monoxide sensor, a smoke detector, a gas toxicity monitor, a carcinogen detector, a radiation sensor, a location sensor, a location beacon, an object identifier beacon, a telecommunications signal sensor, a sound amplitude sensor, a frequency sensor, an accelerometer, a proximity sensor, a weather sensor, or a seismic sensor.

8. The method of claim 1, wherein the one or more first external IoT-capable devices further comprise at least one of a medical server, a medical database, a user device associated with a physician, a user device associated with a healthcare provider, a user device associated with the user, a user device associated with a relative or guardian of the user, a user device associated with a member of an organization with which the user is affiliated, a user device associated with an emergency response team member, an IoT management node, an IoT human interface device, one or more household devices, one or more office devices, one or more display devices, or one or more communications systems.

9. The method of claim 1, further comprising:
receiving, with at least one of the processor of the first IoT-capable personal tracking device, a processor of each of one or more second IoT-capable personal tracking devices, or a processor of a remote computing system, at least one fourth sensor data from each of at least one fourth sensor of a plurality of fourth sensors of each of the one or more second IoT-capable personal tracking devices that are separate from the first IoT-capable personal tracking device, wherein the plurality of fourth sensors comprises at least one of one or more fifth sensors that monitor physical conditions of the body of the user or one or more sixth sensors that monitor environmental conditions external to the body of the user;

analyzing, with the at least one of the processor of the first IoT-capable personal tracking device, the processor of each of the one or more second IoT-capable personal tracking devices, or the processor of the remote computing system, a combination of the at least one first sensor data and the at least one fourth sensor data to identify one or more second external IoT-capable devices with which to interact and to determine one or more second tasks to be performed by the identified one or more second external IoT-capable devices, each based at least in part on the at least one first sensor data from the at least one first sensor of the first IoT-capable personal tracking device and the at least one fourth sensor data from each of the at least one fourth sensor of each of the one or more second IoT-capable personal tracking devices; and autonomously sending, by the at least one of the processor of the first IoT-capable personal tracking device, the processor of each of the one or more second IoT-capable personal tracking devices, or the processor of the remote computing system and via machine-to-machine communication, one or more second control instructions to each of the identified one or more second external IoT-capable devices, based on the determined one or more second tasks.

10. The method of claim 9, wherein at least one of the one or more first external IoT-capable devices and at least one of the one or more second external IoT-capable devices are the same external IoT-capable device.

11. The method of claim 9, wherein the remote computing system comprises at least one of a gateway device, a cloud computing system, a server in a network, a computing node in the network, or a remote computing system at a customer premises associated with the user.

12. A personal tracking device, comprising:
at least one processor;
a transceiver;
a plurality of first sensors, the plurality of first sensors comprising at least one of one or more second sensors that monitor physical conditions of a body of a user or one or more third sensors that monitor environmental conditions external to the body of the user; and
a non-transitory computer readable medium communicatively coupled to the at least one processor, the non-transitory computer readable medium having stored thereon computer software comprising a set of instructions that, when executed by the at least one processor, causes the personal tracking device to:

receive at least one sensor data from each of at least one sensor of a plurality of first sensors;

analyze the at least one sensor data to identify one or more external Internet of Things ("IoT") -capable devices with which to interact and to determine one or more tasks to be performed by the identified one or more external IoT-capable devices, each based at least in part on the at least one sensor data from each of the at least one sensor, wherein the one or more first external IoT-capable devices are separate from the personal tracking devices and wherein the one or more first external IoT-capable devices comprise at least one of a wearable drug delivery device, an implantable drug delivery device, a smart medical alert bracelet, an IoT vehicle node, one or more lighting systems, one or more environmental control systems, one or more speakers, or one or more security control systems; and autonomously send, via machine-to-machine communication through the transceiver, one or more control instructions to each of the identified one or more external IoT-capable devices, based on the determined one or more tasks.

13. The personal tracking device of claim 12, wherein the personal tracking device is a wearable device.

14. The personal tracking device of claim 13, wherein the wearable device comprises at least one of a wrist strap, a clip, a pin, a clasp, an ear-loop, a finger ring, a toe ring, a bangle, a hook and loop-type strap, eyewear stems, a head band, or a buckle that allows the personal tracking device to be removably affixed to at least one of a portion of skin of the user, a limb of the user, an appendage of the user, a torso of the user, a head of the user, or a piece of clothing worn by the user.

15. The personal tracking device of claim 12, wherein the personal tracking device is an implantable device.

16. The personal tracking device of claim 15, wherein the implantable device comprises at least one of an encapsulation layer, a membrane, a hypo-allergenic housing, a capsule, or casing that allows the personal tracking device to be at least one of implanted under one or more layers of skin of the user, implanted within an organ of the user, implanted within a torso of the user, implanted within a head of the user, implanted within a spine of the user, implanted in an internal cavity of the user, or implanted in an external cavity of the user.

17. The personal tracking device of claim 12, wherein the one or more second sensors comprise at least one of a heart rate monitor, a pulse oximeter, an oximeter, a blood glucose monitor, a blood pressure monitor, a blood flow monitor, a nitrogen monitor, a carbon dioxide monitor, a sleep monitor, an activity monitor, a step counter, one or more limb movement monitors, one or more thermometers, one or more accelerometers, one or more gyroscopes, one or more body fat monitors, one or more body muscle monitors, one or more bone density monitors, one or more pH monitors, a body fluid monitor, a brain wave monitor, a synaptic activity monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a pathogen detector, a blood tester, one or more blood alcohol level detectors, one or more drug testers, or one or more location monitors.

18. The personal tracking device of claim 12, wherein the one or more third sensors comprise at least one of an ambient temperature sensor, a flame detector, a particulate sensor, a light sensor, a humidity sensor, an air quality sensor, an atmospheric oxygen level monitor, an atmospheric carbon dioxide level monitor, an atmospheric nitrogen level monitor, an atmospheric pressure sensor, an environmental carbon monoxide sensor, a smoke detector, a gas toxicity monitor, a carcinogen detector, a radiation sensor, a location sensor, a location beacon, an object identifier beacon, a telecommunications signal sensor, a sound amplitude sensor, a frequency sensor, an accelerometer, a proximity sensor, a weather sensor, or a seismic sensor.

19. The personal tracking device of claim 12, wherein the one or more external IoT-capable devices further comprise at least one of a medical server, a medical database, a user device associated with a physician, a user device associated with a healthcare provider, a user device associated with the user, a user device associated with a relative or guardian of the user, a user device associated with a member of an organization with which the user is affiliated, a user device associated with an emergency response team member, an IoT management node, an IoT human interface device, one or more household devices, one or more office devices, one or more display devices, or one or more communications systems.

20. A system, comprising:
a first personal tracking device, comprising:
at least one first processor;
a first transceiver;
a plurality of first sensors, the plurality of first sensors comprising at least one of one or more second sensors that monitor physical conditions of a body of a user or one or more third sensors that monitor environmental conditions external to the body of the user; and
a first non-transitory computer readable medium communicatively coupled to the at least one first processor, the first non-transitory computer readable medium having stored thereon computer software comprising a first set of instructions that, when executed by the at least one first processor, causes the first personal tracking device to:
receive at least one first sensor data from each of at least one first sensor of the plurality of first sensors;
analyze the at least one first sensor data to identify one or more first external Internet of Things ("IoT") -capable devices with which to interact and to determine one or more first tasks to be performed by the identified one or more first external IoT-capable devices, each based at least in part on the at least one first sensor data from each of the at least one first wherein the one or more first external IoT-capable devices are separate from the personal tracking devices and wherein the one or more first external IoT-capable devices comprise at least one of a wearable drug delivery device, an implantable drug delivery device, a smart medical alert bracelet, an IoT vehicle node, one or more lighting systems, one or more environmental control systems, one or more speakers, or one or more security control systems; and
autonomously send, via machine-to-machine communication through the first transceiver, one or more first control instructions to each of the identified one or more first external IoT-capable devices, based on the determined one or more first tasks; and the one or more first external IoT-capable devices, each comprising:
  a second transceiver;
  at least one second processor; and
  a second non-transitory computer readable medium communicatively coupled to the at least one second processor, the second non-transitory computer readable medium having stored thereon computer software comprising a second set of instructions that, when executed by the at least one second processor, causes the first external IoT-capable devices to:
    receive, via the second transceiver, the first control instructions from the first personal tracking device; and
    perform at least one first task of the first external IoT-capable device based on the first control instructions.

21. The system of claim 20, wherein the first personal tracking device is a wearable device, wherein the wearable device comprises at least one of a wrist strap, a clip, a pin, a clasp, an ear-loop, a finger ring, a toe ring, a bangle, a hook and loop-type strap, eyewear stems, a head band, or a buckle that allows the first personal tracking device to be removably affixed to at least one of a portion of skin of the user, a limb of the user, an appendage of the user, a torso of the user, a head of the user, or a piece of clothing worn by the user.

22. The system of claim 20, wherein the first personal tracking device is an implantable device, wherein the implantable device comprises at least one of an encapsulation layer, a membrane, a hypo-allergenic housing, a capsule, or casing that allows the first personal tracking device to be at least one of implanted under one or more layers of skin of the user, implanted within an organ of the user, implanted within a torso of the user, implanted within a head of the user, implanted within a spine of the user, implanted in an internal cavity of the user, or implanted in an external cavity of the user.

23. The system of claim 20, wherein the one or more second sensors comprise at least one of a heart rate monitor, a pulse oximeter, an oximeter, a blood glucose monitor, a blood pressure monitor, a blood flow monitor, a nitrogen monitor, a carbon dioxide monitor, a sleep monitor, an activity monitor, a step counter, one or more limb movement monitors, one or more thermometers, one or more accelerometers, one or more gyroscopes, one or more body fat monitors, one or more body muscle monitors, one or more bone density monitors, one or more pH monitors, a body fluid monitor, a brain wave monitor, a synaptic activity monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a pathogen detector, a blood tester, one or more blood alcohol level detectors, one or more drug testers, or one or more location monitors.

24. The system of claim 20, wherein the one or more third sensors comprise at least one of an ambient temperature sensor, a flame detector, a particulate sensor, a light sensor, a humidity sensor, an air quality sensor, an atmospheric oxygen level monitor, an atmospheric carbon dioxide level monitor, an atmospheric nitrogen level monitor, an atmospheric pressure sensor, an environmental carbon monoxide sensor, a smoke detector, a gas toxicity monitor, a carcinogen detector, a radiation sensor, a location sensor, a location beacon, an object identifier beacon, a telecommunications signal sensor, a sound amplitude sensor, a frequency sensor, an accelerometer, a proximity sensor, a weather sensor, or a seismic sensor.

25. The system of claim 20, wherein the one or more first external IoT-capable devices further comprise at least one of a medical server, a medical database, a user device associated with a physician, a user device associated with a healthcare provider, a user device associated with the user, a user device associated with a relative or guardian of the user, a user device associated with a member of an organization with which the user is affiliated, a user device associated with an emergency response team member, an IoT management node, an IoT human interface device, an IoT vehicle node, one or more household devices, one or more office devices, one or more display devices, or one or more communications systems.

26. The system of claim 20, further comprising:
  one or more second personal tracking devices that are separate from the IoT-capable personal tracking device, each second personal tracking device comprising:
    at least one third processor;
    a third transceiver;
    a plurality of fourth sensors, the plurality of fourth sensors comprising at least one of one or more fifth sensors that monitor physical conditions of a body of a user or one or more sixth sensors that monitor environmental conditions external to the body of the user; and
    a third non-transitory computer readable medium communicatively coupled to the at least one third processor, the third non-transitory computer readable medium having stored thereon computer software comprising a third set of instructions that, when executed by the at least one third processor, causes the second personal tracking device to:
      receive at least one fourth sensor data from each of at least one fourth sensor of a plurality of fourth sensors; and
      send, via machine-to-machine communication through the third transceiver, the at least one fourth sensor data to at least one of the first personal tracking device or one or more other second personal tracking devices;
  wherein at least one of the first set of instructions, when executed by the at least one first processor, further causes the first personal tracking device or the third set of instructions, when executed by the at least one third processor, further causes one or more of the second personal tracking devices to:
    receive the at least one fourth sensor data from each of the at least one fourth sensor of the plurality of fourth sensors of each of the one or more second IoT-capable personal tracking devices;
    analyze a combination of the at least one first sensor data and the at least one fourth sensor data to identify one or more second external IoT-capable devices with which to interact and to determine one or more second tasks to be performed by the identified one or more second external IoT-capable devices, each based at least in part on the combination of the at least one first sensor data from the at least one first sensor of the first IoT-capable personal tracking device and the at least one fourth sensor data from each of the at least one fourth sensor of each of the one or more second IoT-capable personal tracking devices; and
    autonomously send, via machine-to-machine communication, one or more second control instructions to each of the identified one or more second external IoT-capable devices, based on the determined one or more second tasks.

27. The system of claim 20, further comprising:
a remote computing system, comprising:
  at least one fourth processor; and
  a fourth non-transitory computer readable medium communicatively coupled to the at least one fourth processor, the fourth non-transitory computer readable medium having stored thereon computer software comprising a fourth set of instructions that, when executed by the at least one fourth processor, causes the remote computing system to:
    receive the at least one first sensor data from each of the at least one first sensor of the plurality of first sensors of the first personal tracking device;
    analyze the at least one first sensor data to identify one or more third external IoT-capable devices with which to interact and to determine one or more third tasks to be performed by the identified one or more third external IoT-capable devices, each based at least in part on the at least one first sensor data from each of the at least one first sensor; and
    autonomously send, via machine-to-machine communication, one or more third control instructions to each of the identified one or more third external IoT-capable devices, based on the determined one or more third tasks.

28. The system of claim 27, wherein the remote computing system comprises at least one of a gateway device, a cloud computing system, a server in a network, a computing node in the network, or a remote computing system at a customer premises associated with the user.

* * * * *